United States Patent [19]

Tanaka et al.

[11] Patent Number: 4,557,753
[45] Date of Patent: Dec. 10, 1985

[54] HERBICIDAL 4-BENZOYL-1-METHYL-5-PHENYLALKOXY PYRAZOLES

[75] Inventors: Norio Tanaka; Masakazu Taniguchi, both of Funabashi; Masatoshi Baba, Narashino; Takashi Ikai, Tokyo; Tsutomu Nawamaki, Yono; Masaji Matsunaga, Funabashi, all of Japan

[73] Assignee: Nissan Chemical Industries Ltd., Tokyo, Japan

[21] Appl. No.: 485,832

[22] Filed: Apr. 18, 1983

[30] Foreign Application Priority Data

Apr. 24, 1982 [JP] Japan .................. 57-69351

[51] Int. Cl.$^4$ .................. A01N 43/56; C07D 231/20
[52] U.S. Cl. .................. 71/92; 548/374; 548/377
[58] Field of Search .................. 548/374, 375, 377; 71/92

[56] References Cited

FOREIGN PATENT DOCUMENTS

| | | | |
|---|---|---|---|
| 33454 | 3/1980 | Japan | 71/92 |
| 33455 | 3/1980 | Japan | 71/92 |
| 35036 | 3/1980 | Japan | 71/92 |
| 83752 | 6/1980 | Japan | 71/92 |

*Primary Examiner*—Richard A. Schwartz
*Assistant Examiner*—Kurt G. Briscoe
*Attorney, Agent, or Firm*—Quaintance, Murphy & Presta

[57] ABSTRACT

Pyrazole derivatives, preparations thereof, selective herbicidal compositions containing said derivatives and the use of said derivatives are provided. The pyrazole derivatives having selective herbicidal activity are represented by the formula I:

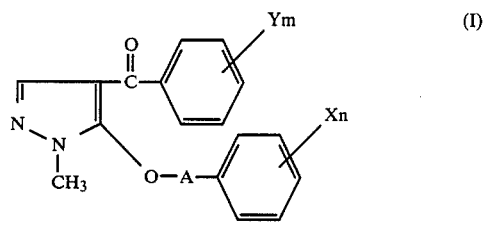

wherein, A denotes a straight or branched lower alkylene or lower alkylidene group; X denotes a halogen atom, nitro group, a lower alkyl group, a lower haloalkyl group, a lower alkoxy group, a lower haloalkoxy group, a lower alkenyl group, phenyl group, cyano group, phenoxy group, a lower alkoxycarbonyl group, an aliphatic or aromatic acyl group, methanesulfonyloxy group or group

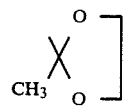

and n is 0 or an integer of 1 to 5, said Xs being the same or different when n is an integer of 2 to 5; and Y denotes a halogen atom, a lower alkyl group, nitro group, phenyl group, a lower alkoxy group or trifluoromethyl group and m is in integer of 1 to 3, said Ys being the same or different when m is 2 or 3.

23 Claims, No Drawings

HERBICIDAL 4-BENZOYL-1-METHYL-5-PHENYLALKOXY PYRAZOLES

BACKGROUND OF THE INVENTION (1) Field of the Invention

This invention relates to a novel pyrazole derivatives, method for preparation thereof, a selective herbicidal composition containing as an active ingredient one or more of said derivatives, and method for damaging and controlling weeds using said derivatives.

(2) Description of the Prior Art

Hitherto, some pyrazole derivatives having herbicidal activity has been known. For example, Japanese Patent Publication No. 36648/79 (corresponding to U.S. Pat. Nos. 4,063,925 and 4,146,726) and Japanese Laid-open Patent Publication No. 41872/79 (corresponding to U.S. Pat. No. 4,230,481) disclose certain 4-benzoyl derivatives of pyrazole which are useful for herbicids.

Among these pyrazole derivatives, however, only the pyrazolate represented by the formula below is used practically and commercially as an active ingredient of a herbicide for use in a paddy field as far as the present inventors' knowledge is concerned.

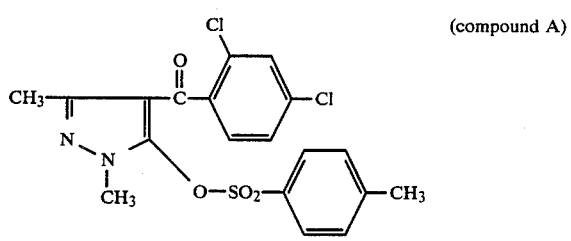
(compound A)

All the pyrazole derivatives disclosed by the above-mentioned publication No. 41872/79 have a lower alkyl group, specifically $CH_3$ group, at 3-position of the pyrazole ring.

Also the majority of the pyrazole derivatives disclosed by the above-mentioned publication No. 36648/79 have a lower alkyl at the 3-position of the pyrazole ring and —OH, —SH, a salt thereof or an organic acid ester thereof at 5-position of said ring; among the pyrazole derivatives disclosed by said publication, only the compound of the following formula is exemplified as a pyrazole derivative having hydrogen atom at 3-position (i.e. unsubstituted at 3-position) of the pyrazole ring:

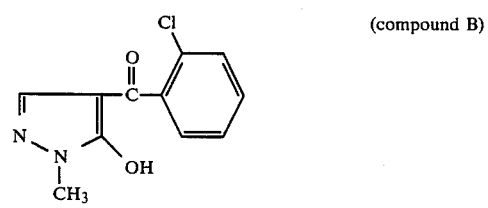
(compound B)

The compound B, however, is inferior to the commercialized compound A in herbicidal activity as is apparent from the biological test data given in the above-mentioned publication No. 36648/79.

Despite the fact that a number of pyrazole derivatives have been synthesized and the herbicidal activity thereof has been tested, there has not been found a pyrazole derivative which is unsubstituted at 3-position of the pyrazole ring and which exhibits herbicidal activity except the above-mentioned compound B.

This is because synthesis of pyrazole derivatives unsubstituted at 3-position has been very difficult while a pyrazole derivative substituted by an alkyl at 3-position has been relatively readily prepared, and because the former compound has been believed to be less active in herbicidal action and thus less practical than the latter one.

The present inventors have done intensive researches on pyrazole derivatives having hydrogen atom at 3-position of the pyrazole ring and have unexpectedly found that some of these pyrazole derivatives exhibit herbicidal action against a wide range of weeds, particularly against perennial weeds such as perennial flat sedge (*Cyperus serotinus*), bulrush (*Scirpus hotarui*) and perennial spikerush (*Eleocharis kuroguwai*) which have been difficult to control and against which no useful herbicide has been developed. Moreover, the present inventors have found a process for readily preparing such pyrazole derivatives to complete the present invention. The compounds according to the present invention have no phytotoxicity upon a paddy-rice plant and, thus, can be used with safety.

SUMMARY OF THE INVENTION

An object of the present invention is to provide a novel pyrazole derivative having strong herbicidal action against weeds, particularly against weeds in paddy field which have not been easily controlled.

Another object of the invention is to provide a process for preparing the above-mentioned novel pyrazole derivative.

Further object of the invention is to provide a selective herbicidal composition contaning one or more of such pyrazole derivative(s) as an active ingredient.

Other objects and features of the invention will be apparent from the description hereinbelow.

The pyrazole derivatives according to the present invention are represented by the formula I:

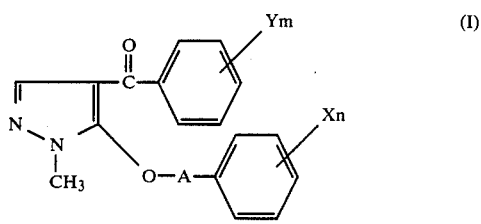
(I)

wherein, A denotes a straight or branched lower alkylene or lower alkylidene group; X denotes a halogen atom, nitro group, a lower alkyl group, a lower haloalkyl group, a lower alkoxy group, a lower haloalkoxy group, a lower alkenyl group, phenyl group, cyano group, phenoxy group, a lower alkoxycarbonyl group, an aliphatic or aromatic acyl group, methanesulfonyloxy group or group

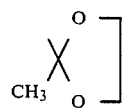

and n is 0 or an integer of 1 to 5, said Xs being the same or different when n is an integer of 2 to 5; and Y denotes a halogen atom, a lower alkyl group, nitro group, phenyl group, a lower alkoxy group or trifluoromethyl group and m is an integer of 1 to 3, said Ys being the same or different when m is 2 or 3.

The pyrazole derivatives of the formula I may be prepared by any of the following methods:

(1) reacting a compound of the formula II:

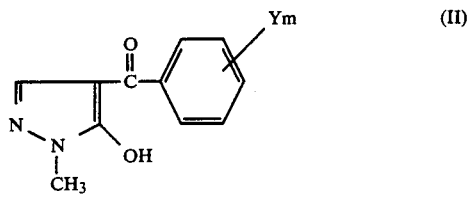

(wherein Y and m are as defined above) with a compound of the formula III:

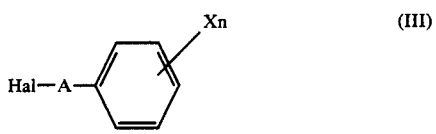

(wherein, Hal denotes a halogen atom and X and n are as defined above) in an inert solvent in the presence of a dehydrohalogenating agent, or (2) halogenating a compound of the formula II:

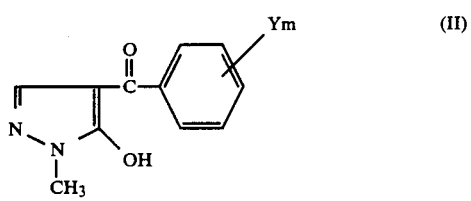

(wherein Y and m are as defined above) by using a halogenating agent, and then reacting the resulting compound with a compound of the formula IV:

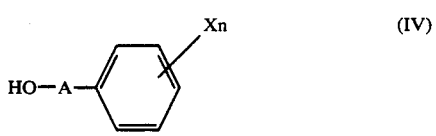

(wherein A, X and n are as defined above), in an inert solvent in the presence of a basic substance, or (3) reacting a compound of the formula II:

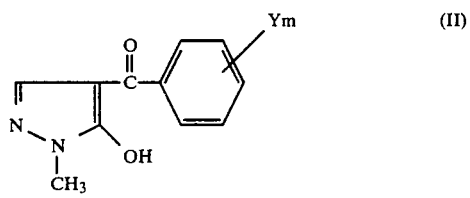

(wherein Y and m are as defined above) with a compound of the formula V:

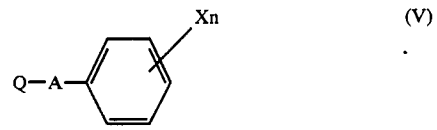

(wherein Q denotes a lower alkylsulfonyloxy group or arylsulfonyloxy group and A, X and n are as defined above).

A selective herbicidal composition according to the present invention contains as an active ingredient an effective amount of one or more of the compounds of the formula I together with a carrier therefor.

A method for destroying and controlling weeds comprises applying to the weeds or locus thereof an effective amount of the compound of the formula I.

DETAILED DESCRIPTION OF THE INVENTION

In the formula I, A is preferably either a straight or branched alkylene group having 1 to 4 carbon atoms, particularly 1 to 3 carbon atoms such as methylene, ethylene or trimethylene, or a straight or branched alkylidene group having 2 to 5 carbon atoms, particularly 2 to 4 carbon atoms such as ethylidene, propylidene, isopropylidene, n-butylidene, 2-methyl-propylidene or sec.-butylidene). Group A is more preferably methylene or ethylidene, and most preferably methylene.

X is preferably a halogen atom such as fluorine, chlorine or bromine; nitro group; a straight or branched alkyl group having 1 to 4 carbon atoms such as methyl, ethyl, n-propyl, isopropyl, n-butyl, sec-butyl or tert-butyl; a straight or branched alkyl group substituted by one or more of halogen atom(s) (i.e. haloalkyl) and having 1 to 3 carbon atoms, particularly one carbon atom such as chloromethyl, bromomethyl, trifluoromethyl; a straight or branched alkoxy group having 1 to 4 carbon atoms such as methoxy, ethoxy, propoxy, isopropoxy, n-butoxy, sec-butoxy or tert-butoxy, particularly methoxy or ethoxy; a straight or branched alkoxy group substituted by one or more of halogen atom(s) (i.e. haloalkoxy) and having 1 to 4 carbon atoms, particularly 1 to 2 carbon atom(s) such as difluoromethoxy, difluorobromomethoxy, 2,2,2-trifluoroethoxy; a straight or branched alkenyl group having one double bond and containing 2 to 4 carbon atoms, particularly 2 or 3 carbon atoms such as ethenyl (=vinyl), n-propenyl, 2-propenyl (=allyl) or 1-methylvinyl, and more particularly ethenyl; phenyl group; —CN group; phenoxy group; a straight or branched lower alkoxycarbonyl group having 2 to 4 carbon atoms in all, particularly 2 or 3 carbon atoms in all such as methoxy carbonyl or ethoxycarbonyl; a straight or branched alkanoyl group (i.e. aliphatic acyl group) having 2 to 5 carbon atoms in all such as acetyl, propionyl, n-butyryl, isobutyryl, valeryl, isovaleryl, —CO—C(CH$_3$)$_3$, particularly acetyl; an aromatic acyl group, particularly benzoyl; methanesulfonyloxy group; or group

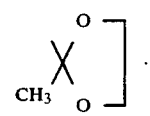

Among these group, more preferred as group X is fluorine, chlorine, methyl or acetyl group.

n is preferably 0, 1, 2 or 3, more preferably 0 or 1.

Y is preferably a halogen atom such as fluorine, chlorine or bromine, particularly chlorine; a straight or branched alkyl group having 1 to 3 carbon atoms such as methyl, ethyl, n-propyl or isopropyl, particularly methyl; nitro group; phenyl group; a straight or branched alkoxy group having 1 to 3 carbon atoms such as methoxy, ethoxy, n-propoxy or isopropoxy, particularly methoxy or ethoxy; or trifluoromethyl group. Among these group, more preferred as group Y is chlorine, methyl, nitro or trifluoromethyl group.

m is preferably 2 or 3.

The first group of the preferred compounds of the formula I is represented by the formula IA:

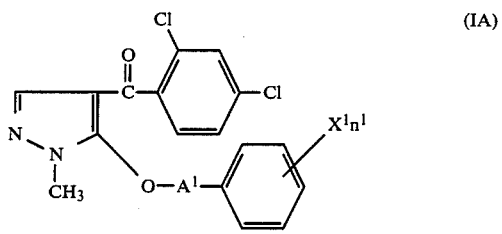
(IA)

wherein, $A^1$ denotes a straight or branched lower alkylene or lower alkylidene group, $X^1$ denotes a halogen atom, nitro group or a lower alkyl group and $n^1$ is 0 or an integer of 1 to 5, said $X^1$s being the same or different when $n^1$ is an integer of 2 to 5.

In the formula IA, $A^1$ is preferably either a straight or branched alkylene group having 1 to 4 carbon atoms, particularly 1 to 3 carbon atoms such as those described in terms of A, and more particularly methylene; or a straight or branched alkylidene group having 2 to 4 carbon atoms, particularly 2 or 3 carbon atoms such as ethylidene, n-propylidene, isopropylidene, and more particularly ethylidene.

$X^1$ is preferably a halogen atom particularly fluorine, chlorine or bromine; a straight or branched alkyl group having 1 to 4 carbon atoms such as those described in terms of X, particularly methyl, ethyl, isopropyl or tert-butyl; or nitro group.

More preferred compounds of the formula IA are those wherein $A^1$ is methylene, $X^1$ is chlorine, nitro or methyl and $n^1$ is 0, 1 or 2.

Most preferred compounds of the formula IA are those wherein $A^1$ is methylene, $X^1$ is chlorine and $n^1$ is 0 or 1.

The second group of the preferred compounds of the formula I is represented by the formula IB:

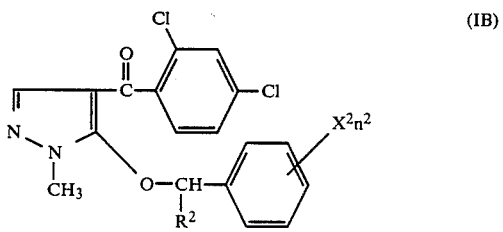
(IB)

wherein, $R^2$ denotes hydrogen atom or a lower alkyl group; and $X^2$ denotes a lower haloalkyl group, a lower alkoxy group, a lower haloalkoxy group, a lower alkenyl group, phenyl group, cyano group, phenoxy group, a lower alkoxycarbonyl group, an aliphatic or aromatic acyl group, methanesulfonyloxy group or a group

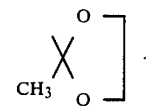

and $n^2$ is an integer of 1 to 3, $X^2$s being the same or different when $n^2$ is 2 or 3.

In the formula IB, $R^2$ is preferably hydrogen atom or a straight or branched alkyl group having 1 to 4 carbon atoms such as those described in terms of X, and particularly hydrogen atom.

$X^2$ is preferably a straight or branched lower alkyl group substituted by one or more halogen atoms such as fluorine, chlorine or bromine, (i.e. haloalkyl) and having 1 to 3 carbon atom(s), particularly halogenated methyl such as chloromethyl, bromomethyl or trifluoromethyl; a straight or branched alkoxy group having 1 to 4 carbon atoms such as those described in terms of X, particularly methoxy or ethoxy group; a straight or branched alkoxy group substituted by one or more of halogen atom(s) such as fluorine, chlorine or bromine (i.e. haloalkoxy) and having 1 to 4 carbon atoms, particularly 1 to 2 carbon atom(s) such as difluoromethoxy or 2,2,2-trifluoroethoxy; a straight or branched alkenyl group having one double bond and containing 2 to 4 carbon atoms, particularly 2 or 3 carbon atoms such as those mentioned in terms of X, and more particularly ethenyl; phenyl group; cyano group; phenoxy group; a straight or branched lower alkoxycarbonyl group having 2 to 4 carbon atoms in all, particularly 2 or 3 carbon atoms in all such as methoxycarbonyl or ethoxycarbonyl; a straight or branched alkanoyl group (i.e. aliphatic acyl group) having 2 to 5 carbon atoms in all such as those mentioned in terms of X, particularly acetyl; an aromatic acyl group, particularly benzoyl; methane sulfonyloxy group; or a group

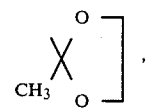

$n^2$ is preferably 1.

Among the compounds of the formula IA, more preferred are those wherein $R^2$ is hydrogen, $X^2$ is bromomethyl, trifluoromethyl, methoxy, ethoxy, difluoromethoxy, 2,2,2-trifluoroethoxy, ethenyl, phenyl, cyano, phenoxy, ethoxycarbonyl, acetyl, methanesulfonyl or

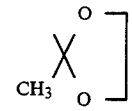

and $n^2$ is 1. Most preferred compounds of the formula IA are those wherein $R^2$ is hydrogen, $X^2$ is acetyl group, and $n^2$ is 1.

The third group of the preferred compounds of the formula I is represented by the formula IC:

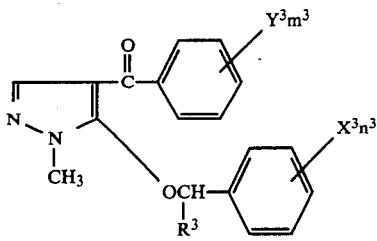

(IC)

wherein, $R^3$ denotes hydrogen atom or a lower alkyl group; $X^3$ denotes a halogen atom, a lower alkyl group, a lower haloalkyl group, a lower alkoxy group, a lower haloalkoxy group, a lower alkenyl group, or nitro group and $n^3$ is 0 or an integer of 1 to 3, said $X^3$s being the same or different when $n^3$ is 2 or 3; and $Y^3$ is a halogen atom, a lower alkyl group, nitro group, phenyl group, a lower alkoxy group, or trifluoromethyl group and $m^3$ is an integer of 1 to 3, said $Y^3$s being the same or different when $m^3$ is 2 or 3.

In the formula IC, $R^3$ is preferably either hydrogen atom, or a straight or branched alkyl group having 1 to 3 carbon atoms, particularly 1 or 2 carbon atom(s) such as methyl or ethyl, and more particularly methyl.

$X^3$ is preferably a halogen atom such as fluorine, chlorine or bromine, particularly chlorine or bromine; a straight or branched lower alkyl group having 1 to 3 carbon atoms, particularly methyl; a straight or branched lower alkyl group substituted by one or more of halogen atom(s) such as fluorine, chlorine or bromine (i.e. haloalkyl) and having 1 to 3 carbon atoms, particularly halogenated methyl such as chloromethyl, bromomethyl or trifluoromethyl, more particularly trifluoromethyl; a straight or branched alkoxy group having 1 to 3 carbon atoms, particularly methoxy or ethoxy; a straight or branched alkoxy group substituted by one or more of halogen atom(s) (i.e. haloalkoxy group) and having 1 to 3 carbon atoms, particularly 1 or 2 carbon atom(s) such as difluoromethoxy, difluorobromomethoxy or 2,2,2-trifluoroethoxy, more particularly difluoromethoxy; a straight or branched alkenyl group having one double bond and containing 2 to 4 carbon atoms such as ethenyl, n-propenyl, allyl, 1 or 2-butenyl, particularly ethenyl; or nitro group.

$n^3$ is preferably 0 or 1.

$Y^3$ is preferably a halogen atom such as fluorine, chlorine or bromine, particularly chlorine; a straight or branched alkyl group having 1 to 3 carbon atoms, particularly methyl; nitro group; phenyl group; a straight or branched alkoxy group having 1 to 3 carbon atoms, particularly methoxy or ethoxy; or trifluoromethyl.

More preferred compounds of the formula IC are those wherein $R^3$ is hydrogen, $X^3$ is chlorine, bromine, methyl, trifluoromethyl, methoxy, difluoromethoxy, ethenyl or nitro, $n^3$ is 0 or 1, $Y^3$ is chlorine, methyl, nitro, or trifluoromethyl and $n^3$ is an integer of 1 to 3.

The most important compounds according to the present invention include the following compounds: 4-(2,4-dichlorobenzoyl)-1-methyl-5-benzyloxypyrazole, 4-(2,4-dichlorobenzoyl)-1-methyl-5-(2-methylbenzyloxy)-pyrazole, 4-(2,4-dichlorobenzoyl)-1-methyl-5-(4-methylbenzyloxy)-pyrazole, 4-(2,4-dichlorobenzoyl)-1-methyl-5-(2-chlorobenzyloxy)-pyrazole, 4-(2,4-dichlorobenzoyl)-1-methyl-5-(4-chlorobenzyloxy)-pyrazole, 4-(2,4-dichlorobenzoyl)-1-methyl-5-(2-fluorobenzyloxy)-pyrazole, 4-(2,4-dichlorobenzoyl)-1-methyl-5-(4-acetylbenzyloxy)-pyrazole and 4-(2,4-dichloro-3-methylbenzoyl)-1-methyl-5-(2-chlorobenzyloxy)-pyrazole.

The compounds of the formula I may be synthesized readily according to the following reaction scheme:

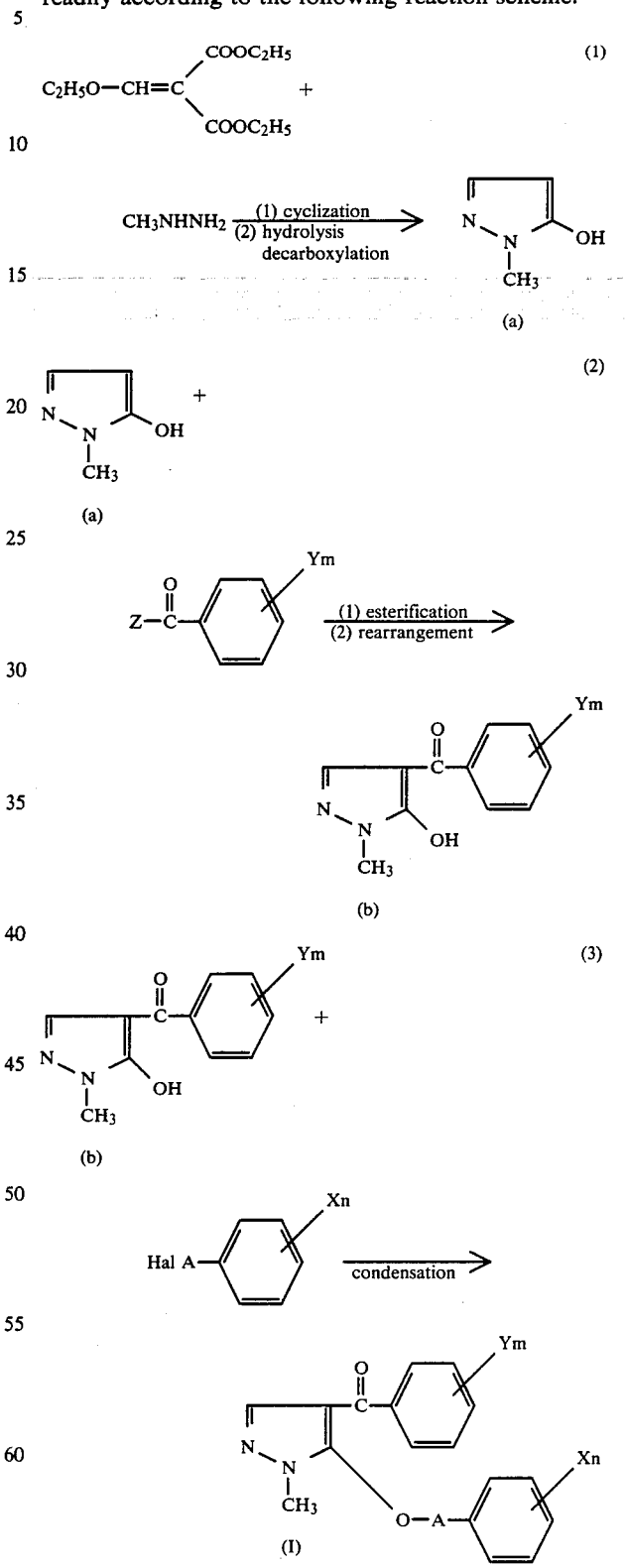

wherein

Z denotes a halogen atom or hydroxyl group, preferably chlorine,

Hal denotes a halogen atom, preferably chlorine or bromine, and A, X, Y, n and m each have the same meanings as defined in formula I.

Reaction (1) represents a reaction series comprising (i) synthesizing 4-carboethoxy-5-hydroxy-1-methylpyrazole from an ethoxymethylene malonate ester and methylhydrazine through cyclization reaction, followed by (ii) hydrolyzing and decarboxylating the resulting compound to obtain 5-hydroxy-1-methylpyrazole. The cyclization reaction is performed at a temperature from −50° to 200° C., preferably from −20° to 100° C. in an inert solvent such as methanol, ethanol, water, dioxane, benzene or toluene.

The hydrolysis and decarboxylation is performed at a temperature from 50° to 150° C., preferably around boiling point of the solvent used in cyclization reaction.

A part of the intermediate compound (b), i.e. 4-(2,4-dichlorobenzoyl)-1-methyl-5-hydroxypyrazole, is a novel compound. The compounds (b) including the above novel compound can be prepared from compound (a) as a starting material through, for example, Reaction (2). For example, compounds (b) may be prepared by reacting compound (a) with a substituted benzoyl halide in an inert solvent in the presence of a dehydrohalogenating agent, preferably such as sodium hydroxide, potassium hydroxide, sodium carbonate or triethylamine to produce the corresponding esters and then effecting rearrangement of the esters to obtain the compounds (b). As the solvent for the esterification reaction may be used, for example, organic solvents such as dioxane, acetonitrile, benzene, toluene or chloroform alone or in combination with each other or with water, namely two phase systems such as water-toluene, water-chloroform and the like. Preferred solvents, however, for the esterification are water-chloroform two phase system. The rearrangement of the ester is performed by heating the ester with potassium carbonate or sodium carbonate in an inert solvent such as dioxane at a temperature from 50° to 150° C.

Reaction (3) represents a condensation reaction of an intermediate (b) with a substituted aralkyl halide to produce the compound of the formula I. This reaction is preferably carried out in a solvent which is inert to the reaction in the presence of a dehydrohalogenating agent. Suitable inert solvents are, for example, ethers such as diethyl ether, tetrahydrofuran and dioxane, aromatic hydrocarbons such as benzene, toluene and xylene, ketones such as acetone, methylethylketone, halogenated hydrocarbons such as dichloromethane, chloroform and carbon tetrachloride, ethyl acetate, N,N-dimethylformamide, acetnitrile and the mixtures thereof. Among these solvents preferred ones are benzene, toluene, acetone and acetonitrile. Suitable dehydrohalogenating agents for Reaction (3) are, for example, inorganic bases such as sodium carbonate, and potassium carbonate, and organic bases such as pyridine, triethylamine and N,N-diethylaniline, and preferably triethylamine. The reaction temperature ranges from room temperature to the boiling point of the solvent employed. However, it is most advantageous to effect the reaction at the boiling point of the solvent from the viewpoint of operation. By selecting the above-mentioned reaction conditions of the condensation reaction (3) appropriately, the compounds of the formula (I) can be obtained in a quite high yield.

Instead of the Reaction (3), the following Reactions (4) and (5) may be used for the synthesis of the compounds according to the present invention.

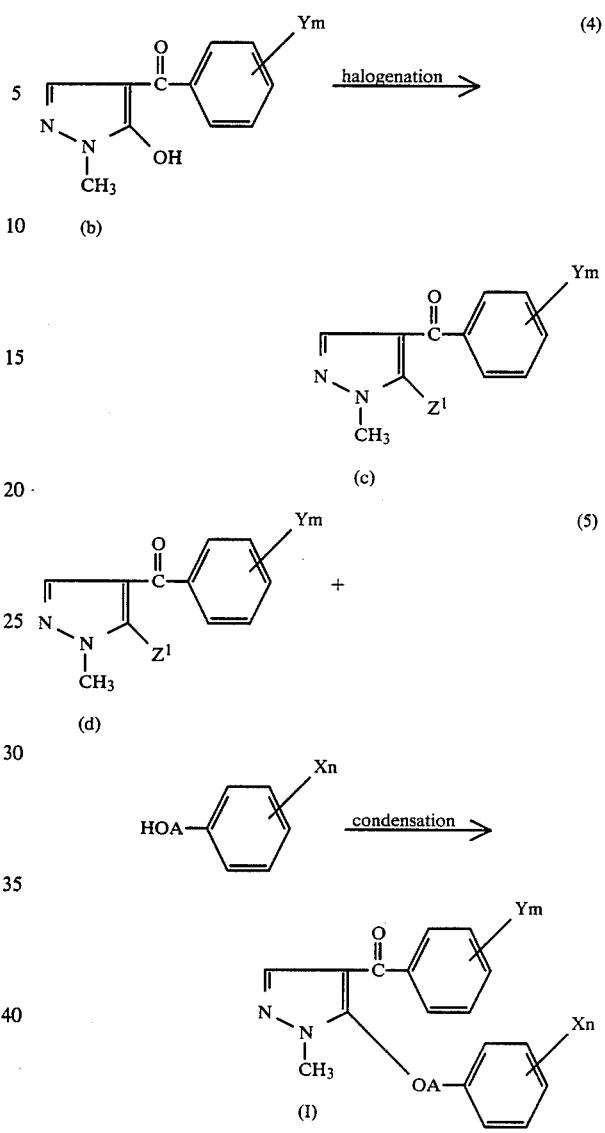

wherein, $Z^1$ denotes a halogen atom, preferably chlorine or bromine atom, and A, X, Y, n and m have the same meanings as previously defined. The compound (b) may be readily converted to the corresponding 5-halogenated pyrazole (c) in a high yield through Reaction (4) by using a halogenating agent. Preferred halogenating agent includes phosphorus oxychloride, phosphorus oxybromide, phosphorus pentachloride, phosphorus pentabromide, triphenylphosphine dichloride and triphenylphosphine dibromide, particularly phosphorus oxychloride, phosphorus oxybromide. The reaction temperature ranges from room temperature to about the boiling point of the reactant or solvent employed. However, good results can be obtained by effecting the reaction at about the boiling point of the reactant or solvent employed.

Reaction (5) represents a condensation reaction of an intermediate compound (c) obtained through Reaction (4) with a substituted aralkylalcohol to obtain the compound of the formula I. This reaction may be accomplished in a good yield by effecting it in an inert solvent and in the presence of an appropriate basic substance. Suitable inert solvents are ethers such as diethyl ether, tetrahydrofuran and dioxane, aromatic hydrocarbons such as benzene and toluene, ketones such as acetone and methylethylketone, N,N-dimethylformamide, hexamethylphosphoric triamide, water and mixtures thereof. Suitable basic substances are sodium hydride, sodium carbonate, potassium carbonate, sodium hydroxide, potassium hydroxide and the like. The reaction temperature for Reaction (5) is not restricted and may range from room temperature to the boiling point of the solvent employed; however, it is preferable to effect the reaction at a temperature of 100° C. or the boiling point of the solvent employed.

Reactions (4) and (5) are used instead of Reaction (3) especially for the synthesis of the compounds of the formula IB. The intermediates (d) which have an alkoxy group at 2-position of the benzoyl moiety may also be synthesized according to the following Reactions (6) and (7):

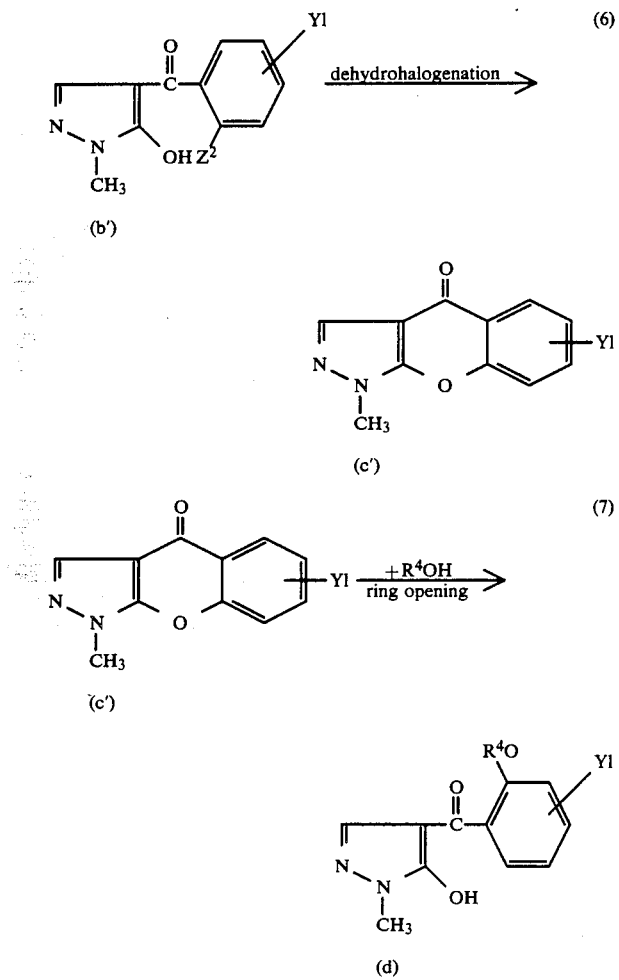

wherein, $Z^2$ denotes a halogen atom such as chlorine or bromine, or nitro group and preferably chlorine, $R^4$ denotes a lower alkyl group, preferably a straight or branched $C_1$ to $C_4$ alkyl group, l denotes 0 or an integer of 1 or 2, and Y has the same meaning as previously defined. A cyclized compound (c') may be readily obtained through Reaction (6) from a compound (b') such as, for example, 4-(2,4-dichlorobenzoyl)-1-methyl-5-hydroxypyrazole by using an appropriate dehydrohalogenating agent such as potassium carbonate, sodium carbonate, potassium hydroxide, sodium hydroxide, triethylamine, or pyridine, preferably potassium carbonate or potassium hydroxide in combination with an inert solvent such as, for example, N,N-dimethylformamide, dimethylsulfoxide, benzene, toluene, preferably N,N-dimethylformamide. The Reaction (6) is preferably effected at the boiling point of the solvent employed or around 100° C.

The cyclized compound (c') may be converted to a compound (d') through ring-opening Reaction (7) by heating the compound (c') to 60° to 70° C. for several hours in an alcohol in the presence of a base. Suitable alcohols as the solvent are methanol, ethanol, isopropylalcohol and preferably ethanol. Suitable bases are causic alkali such as sodium hydroxide and potassium hydroxide.

The compounds (d) may be alternatively prepared by first heating the compound (c') in an aqueous solution of a base such as sodium hydroxide or potassium hydroxide preferably at a temperature of 30° to 100° C. for several hours to convert it to a compound (e) and then reacting the resulting compound (e) with a lower alkyl halide ($R^4Z^3$) according to the following Reaction (8):

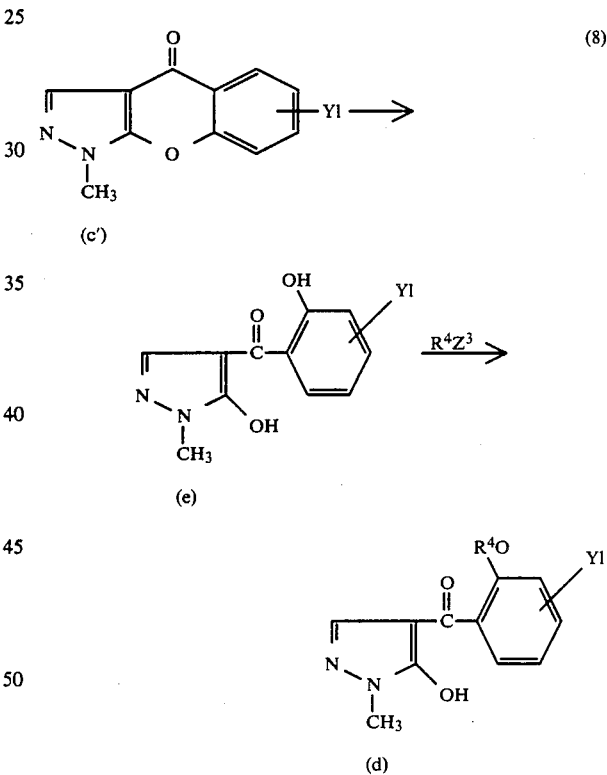

wherein $Z^3$ denotes a halogen atom, preferably chlorine or bromine and Y, $R^4$ and l are as previously defined. The reaction of the compound (e) with a lower alkyl halide is preferably carried out at a temperature of 40° to 200° C. for 0.5 to 20 hours in an inert solvent such as benzene or toluene.

The intermediate compounds (d) which are synthesized according to Reactions (6) and (7) or Reactions (6) and (8) are converted into the compounds of the formula I through Reaction (3) or Reactions (4) and (5).

Alternatively, the compounds of the formula (I) may be prepared according to the following Reaction (9) instead of Reaction (3):

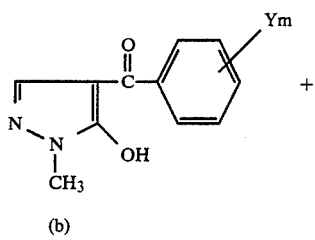

(b)

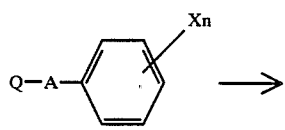

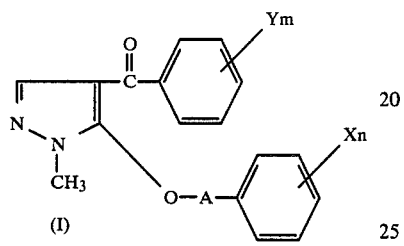

(I)

wherein, Q denotes a straight or branched lower alkylsulfonyloxy group or arylsulfonyloxy group preferably having 1 to 7 carbon atoms, more preferably methanesulfonyloxy group, or p-toluenesulfonyloxy group, and A, X, Y, n and m are as defined previously.

Reaction (9) is preferably effected in an inert solvent such as benzene, toluene, xylene, acetonitrile, acetone, N,N-dimethylformamide and so on. The reaction temperature ranges from room temperature to the boiling point of the solvent employed, and preferably the boiling point of the solvent employed.

The compounds of the formula I or preferred compounds of the formula IA, IB or IC may be prepared according to any of the above-mentioned reactions by using the corresponding starting materials and/or reagents.

Synthesis of the compounds according to the invention is illustrated by way of the following examples which do not restrict the present invention.

SYNTHESIS EXAMPLE 1

Synthesis of 1-methyl-5-hydroxypyrazole

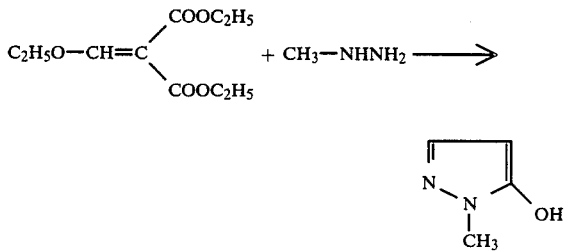

To a mixture of 150 ml of ethanol and 108 g (0.5 mol) of ethoxymethylenemalonate diethyl ester was added dropwise 23 g (0.5 mol) of methylhydrazine at below 0° C. After completion of the addition, the reaction mixture was stirred for 1 hour at room temperature, and then refluxed for 1 hour. Then the reaction mixture was added to 200 ml of concentrated hydrochloric acid and refluxed for 2 hours. After completion of the reaction, the reflux condenser was replaced by a water separator and, after adding butanol, the reaction mixture was subjected to azeotropic dehydration. After completion of the dehydration, butanol in the mixture was distilled off under reduced pressure and the residue was recrystallized from isopropylalcohol to give 38 g (0.38 mol) of the title compound as a hydrochloric salt (yield: 76%), m.p.: 135°–147° C.

SYNTHESIS EXAMPLE 2

Synthesis of 4-(2,4-dichlorobenzoyl)-1-methyl-5-hydroxypyrazole

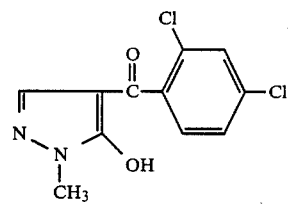

In 30 ml of an aqueous solution containing 4.0 g (0.1 mol) of sodium hydroxide was dissolved 9.8 g (0.1 mol) of 1-methyl-5-hydroxypyrazole at room temperature. To the resulting aqueous solution maintained at 10° C. was added dropwise a solution prepared from 23.0 g (0.11 mol) of 2,4-dichlorobenzoyl chloride and 100 ml of chloroform with stirring over 1 hour, followed by additional stirring for 2 hours at a temperature below about 20° C. Then the chloroform layer was separated and washed successively with water, 5% aqueous sodium bicarbonate and saturated brine and, after drying, solvent was distilled off under reduced pressure to give 23.5 g of 1-methyl-5-(2,4-dichlorobenzoyloxy)-pyrazole (yield: 86%).

Then, 20.3 g (0.075 mol) of the 1-methyl-5-(2,4-dichlorobenzoyloxy)-pyrazole thus obtained was mixed intimately with 20.8 g (0.15 mol) of anhydrous potassium bicarbonate and the resulting mixture was heated gradually. After the reaction mixture was melted and then solidified at about 120° C., it was heated at 130° to 150° C. for additional 2 hours. The reaction mixture was then allowed to cool, added with 50 ml of isopropyl alcohol and refluxed for 1 hour. After cooling, the reaction mixture was added successively with 100 ml of water, hydrochloric acid to acidify the mixture and 200 ml of chloroform and was stirred for a while. The chloroform layer was separated, washed with water and saturated brine and then dried. The solid product which was obtained by evaporation under reduced pressure was recrystallized from 95% ethanol to give 14.4 g of the title compound 4-(2,4-dichlorobenzoyl)-1-methyl-5-hydroxypyrazole as colorless needle-like crystals (yield: 71%), m.p.: 181.0°–181.5° C.

NMR (δ, ppm, CDCl$_3$): 3.68 (3H, s), 7.38–7.61 (4H), 8.01 (1H, s).

SYNTHESIS EXAMPLE 3

Synthesis of
4-(2,4-dichlorobenzoyl)-1-methyl-5-benzyloxypyrazole (Compound No. 1.1)

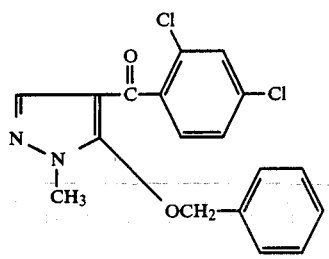

To a mixture of 1.50 g (0.0055 mol) of 4-(2,4-dichlorobenzoyl)-1-methyl-5-hydroxypyrazole, 0.56 g (0.0055 mol) of triethylamine and 30 ml of benzene was added 1.03 g (0.0061 mol) of benzyl bromide and the resulting mixture was heated under reflux for 2 hours with stirring. After cooling, precipitated triethyl amine hydrobromide was filtered off. The filtrate was concentrated under reduced pressure and was subjected to column chromatography (silica gel, using ethyl acetate/benzene 1:3 as an eluent) to give 1.79 g of the title compound 4-(2,4-dichlorobenzoyl)-1-methyl-5-benzyloxypyrazole (yield: 93%).

NMR (δ, ppm, CDCl$_3$): 3.46 (3H, s), 5.51 (2H, s), 7.27–7.43 (9H).

SYNTHESIS EXAMPLE 4

Synthesis of
4-(2,4-dichlorobenzoyl)-1-methyl-5-{2-(4-methylphenyl)ethoxy}-pyrazole (Compound No. 1.17)

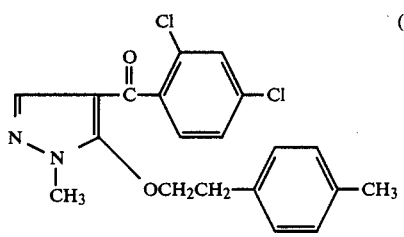

A mixture of 1.36 g (0.005 mol) of 4-(2,4-dichlorobenzoyl)-1-methyl-5-hydroxypyrazole, 0.51 g (0.005 mol) of triethylamine, 1.00 g (0.005 mol) of 2-(4-methylphenyl)ethyl bromide and 30 ml of benzene was heated under reflux for 1 hour.

After cooling, precipitated triethylamine hydrobromide was filtered off. The benzene layer was washed successively with water, and 5% aqueous sodium bicarbonate and, after drying thereof, the solvent was distilled off. The resulting oil (2.15 g) was subjected to column chromatography in the same manner as Synthesis Example 3 to give 2.00 g of the title compound (yield: 92%).

NMR (δ, ppm; CDCl$_3$): 2.29 (3H, s), 3.01 (2H, t, J=7 Hz), 3.43 (3H, s), 4.71 (2H, t, J=7 Hz), 7.10–7.44 (8H).

SYNTHESIS EXAMPLE 5

Synthesis of
4-(2,4-dichlorobenzoyl)-1-methyl-5-(4-nitrobenzyloxy)-pyrazole (Compound No. 1.9)

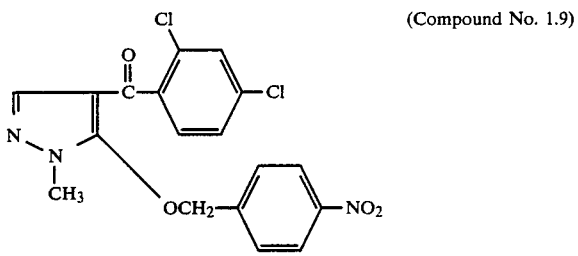

To a mixture of 1.36 g (0.005 mol) of 4-(2,4-dichlorobenzoyl)-1-methyl-5-hydroxypyrazole, 0.51 g (0.005 mol) of triethylamine, 20 ml of benzene and 10 ml of N,N-dimethylformamide was added with stirring 0.86 g (0.005 mol) of 4-nitrobenzyl chloride at room temperature. The resulting mixture was then heated under reflux for 3 hours. After cooling the reaction mixture, the solvent was distilled off under reduced pressure and 30 ml of water and 30 ml of ethyl acetate were added thereto. After stirring the mixture for a while, an organic layer was separated, washed with water and 5% aqueous sodium bicarbonate and dried. Then the solvent was distilled off therefrom. The resulting oil (2.02 g) was subjected to column chromatography (silica gel, eluting with benzene/ethyl acetate 1:1) to give 1.76 g of the title compound (yield 87%), m.p. 116.5°–117.5° C.

NMR (δ, ppm; CDCl$_3$): 3.64 (3H, s), 5.69 (2H, s), 7.32–7.45 (4H), 7.92 (4H, double d).

The compounds listed in Table 1 were synthesized in the same manner as Synthesis Examples 1 through 5. The compounds obtained in Synthesis Examples 3 through 5 are also listed in Table 1.

TABLE 1
The compounds of the formula:
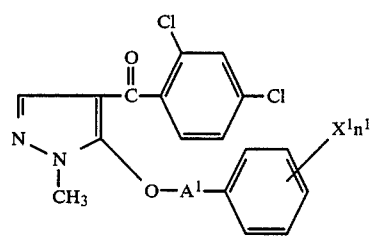
(IA)
| Compound No. | $-A^1$ ⌬ $X^1_{n^1}$ | Appearance or m.p. (°C.) | NMR (δ, ppm, CDCl$_3$) $-N-CH_3$ | $-O-\underline{A}^1$ ⌬ $X^1_{n^1}$ |
|---|---|---|---|---|
| 1.1 | $-CH_2-$⌬ | oil | 3.46 | 5.51 |
| 1.2 | $-CH_2-$⌬$-CH_3$ | oil | 3.39 | 5.44 |
| 1.3 | $-CH_2-$⌬$-CH_3$ (m) | oil | 3.48 | 5.45 |
| 1.4 | $-CH_2-$⌬$-CH_3$ (o) | oil | 3.45 | 5.54 |
| 1.5 | $-CH_2-$⌬$-Cl$ | oil | 3.51 | 5.50 |
| 1.6 | $-CH_2-$⌬$-Cl$ (m) | oil | 3.55 | 5.52 |
| 1.7 | $-CH_2-$⌬$-CH(CH_3)_2$ | oil | 3.44 | 5.45 |
| 1.8 | $-CH_2-$⌬$-C(CH_3)_3$ | oil | 3.45 | 5.46 |
| 1.9 | $-CH_2-$⌬$-NO_2$ | 116.5~117.5 | 3.64 | 5.69 |

TABLE 1-continued
The compounds of the formula:
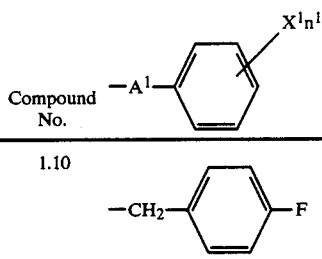
(IA)
| Compound No. | −A¹−⟨⟩−X¹ₙ¹ | Appearance or m.p. (°C.) | NMR (δ, ppm, CDCl₃) |  |
|---|---|---|---|---|
| | | | −N−C$\underline{H}_3$ | −O−$\underline{A}^1$−⟨⟩−X¹ₙ¹ |
| 1.10 | −CH₂−⟨⟩−F | oil | 3.50 | 5.50 |
| 1.11 | −CH₂−⟨⟩−Br | oil | 3.53 | 5.50 |
| 1.12 | −CH₂−⟨⟩ (Br ortho) | oil | 3.56 | 5.60 |
| 1.13 | −CH₂−⟨⟩−Cl,Cl | oil | 3.58 | 5.50 |
| 1.14 | −CH₂−⟨⟩ (2,4-Cl₂) | oil | 3.57 | 5.60 |
| 1.15 | −CH₂−⟨⟩ (2,4-(CH₃)₂) | oil | 3.42 | 5.50 |
| 1.16 | −CH(CH₃)−⟨⟩ | oil | 3.42 | 1.74d 6.09q |
| 1.17 | −CH₂CH₂−⟨⟩−CH₃ | oil | 3.43 | 3.01t 4.71t |

TABLE 1-continued
The compounds of the formula:
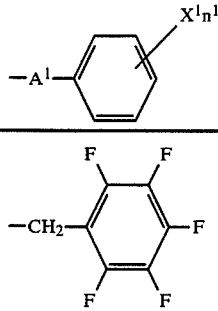
(IA)
| Compound No. | 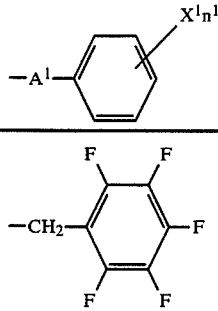 | Appearance or m.p. (°C.) | NMR (δ, ppm, CDCl$_3$) —N—C$\underline{H}_3$ | 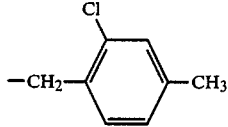 |
|---|---|---|---|---|
| 1.18 | 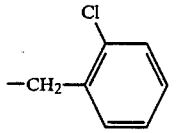 | 111.0~112.0 | 3.59 | 5.72 |
| 1.19 | —CH$_2$—(2-Cl, 4-CH$_3$-C$_6$H$_3$) | oil | 3.50 | 5.53 |
| 1.20 | —CH$_2$—(2-Cl-C$_6$H$_4$) | oil | 3.54 | 5.61 |
| 1.21 | —CH$_2$—(4-C$_2$H$_5$-C$_6$H$_4$) | oil | 3.46 | 5.47 |
| 1.27 | —CH$_2$—(2-F, 6-Cl-C$_6$H$_3$) | oil | 3.49 | 5.71d |
| 1.50 | —CH$_2$—(2-F-C$_6$H$_4$) | oil | 3.53 | 5.60 |
| 1.51 | —CH$_2$—(2-NO$_2$-C$_6$H$_4$) | 110.5~113.5 | 3.66 | 5.87 |

TABLE 1-continued

The compounds of the formula:

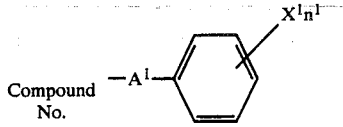
(IA)

| Compound No. | $-A^1$  | Appearance or m.p. (°C.) | NMR (δ, ppm, CDCl₃) $-N-C\underline{H}_3$ | $-O-\underline{A}^1$ 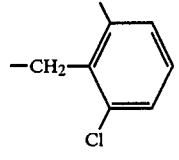 |
|---|---|---|---|---|
| 1.52 | 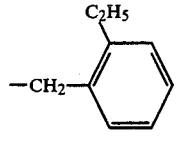 | oil | 3.49 | 5.82 |
| 1.54 | 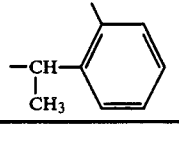 | oil | 3.44 | 5.57 |
| 1.55 | 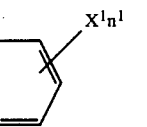 | 174~178 | 3.55 | 1.72d 6.43q |

In accordance with the above-mentioned synthesis examples, the following compounds listed in Table 2 can be synthesized readily.

TABLE 2

The compounds of the formula:

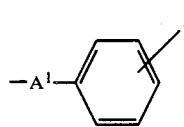
(IA)

| Compound No. | $-A^1$ 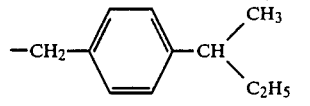 | Compound No. | $-A^1$ 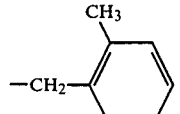 |
|---|---|---|---|
| 1.22 | -CH₂- ⌬ -CH(CH₃)(C₂H₅) | 1.35 | -CH₂- ⌬ (2-CH₃, 4-NO₂) |

TABLE 2-continued

The compounds of the formula:

(IA)

| Compound No. | $-A^1$-Ar($X^1$)$_{n^1}$ | Compound No. | $-A^1$-Ar($X^1$)$_{n^1}$ |
|---|---|---|---|
| 1.23 | $-CH_2-$C$_6$H$_4$-4-$CH_2CH(CH_3)_2$ | 1.36 | $-CH_2-$(2,4,5-trichlorophenyl) |
| 1.24 | $-CH_2-$C$_6$H$_4$-4-$C_3H_7$-n | 1.37 | $-CH_2CH(CH_3)-$C$_6$H$_5$ |
| 1.25 | $-CH_2-$C$_6$H$_4$-4-$C_4H_9$-n | 1.38 | $-CH(CH_3)-CH_2-$C$_6$H$_5$ |
| 1.26 | $-CH_2-$(2,5-dimethylphenyl) | 1.39 | $-CH_2CH_2-$C$_6$H$_4$-4-$NO_2$ |
| 1.28 | $-CH_2-$(2-Cl-4-$NO_2$-phenyl) | 1.40 | $-CH_2CH_2CH_2-$C$_6$H$_5$ |
| 1.29 | $-CH_2-$(2-$NO_2$-5-Cl-phenyl) | 1.41 | $-CH(C_2H_5)-$C$_6$H$_5$ |
| 1.30 | $-CH_2-$(3-$NO_2$-4-Cl-phenyl) | 1.42 | $-CH_2-$C$_6$H$_4$-3-Br |
| 1.31 | $-CH_2-$(2,4-dinitrophenyl) | 1.43 | $-CH_2-$(2,6-dibromophenyl) |

TABLE 2-continued
The compounds of the formula:
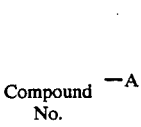
(IA)
| Compound No. | $-A^1$—⟨ ⟩—$X^1{}_{n^1}$ | Compound No. | $-A^1$—⟨ ⟩—$X^1{}_{n^1}$ |
|---|---|---|---|
| 1.32 | 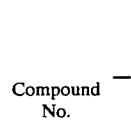 | 1.44 | 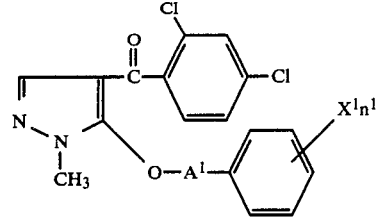 |
| 1.33 | 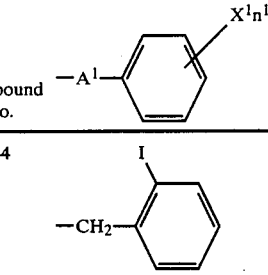 | 1.45 | 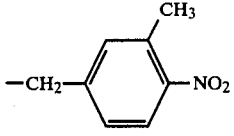 |
| 1.34 | 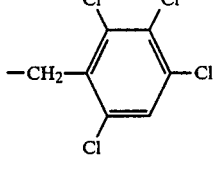 | 1.46 | 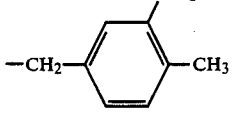 |
| 1.47 | 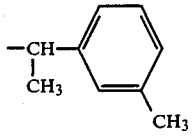 | 1.53 | 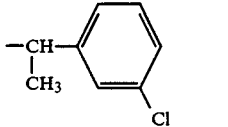 |
| 1.48 | 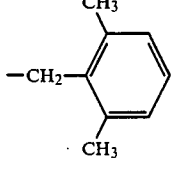 | 1.56 | 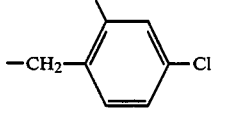 |
| 1.49 | 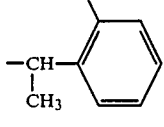 | 1.57 | 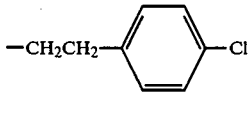 |

SYNTHESIS EXAMPLE 6

Synthesis of 4-(2,4-dichlorobenzoyl)-1-methyl-5-(p-acetylbenzyloxy)pyrazole

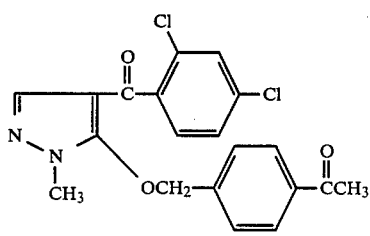

(Compound No. 2.18)

In 30 ml of dry benzene containing 0.50 g (0.005 mol) of triethylamine was dissolved 1.36 (0.005 mol) of 4-(2,4-dichlorobenzoyl)-1-methyl-5-hydroxypyrazole, and then 1.07 g (0.005 mol) of p-acetylbenzylbromide was added thereto. The resulting mixture was heated under reflux for 3 hours. After cooling the reaction mixture, the salt precipitated was filtered off and the solvent was distilled off therefrom under reduced pressure. The resulting oil was purified through column chromatography on silica gel using benzene/ethyl acetate 8:1 as an eluant to give 1.67 g of the title compound (yield 83%).

$^1$H-NMR ($\delta$, ppm, CDCl$_3$): 2.53 (3H, s), 3.54 (3H, s), 5.58 (2H, s), 7.24–7.99 (8H).

SYNTHESIS EXAMPLE 7

Synthesis of 4-(2,4-dichlorobenzoyl)-1-methyl-5-chloropyrazole

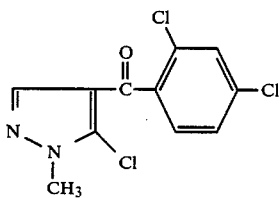

To 5 ml of phosphorus oxychloride was added 2.71 g (0.01 mol) of 4-(2,4-dichlorobenzoyl)-1-methyl-5-hydroxypyrazole and the resulting mixture was heated under reflux for 3 hours. After cooling, the reaction mixture was poured into ice water. Oily product was extracted with ethyl acetate, washed successively with 5% aqueous sodium bicarbonate and saturated brine and dried over anhydrous sodium sulfate. Then the solvent was distilled off therefrom under reduced pressure and the resulting oil was purified through silica gel column chromatography using benzene as an eluant to give 2.84 g of the title compound as pale yellow crystals, (yield: 98%), m.p. 81.0°–83.0° C.

$^1$H-NMR ($\delta$, ppm, CDCl$_3$): 3.84 (3H, s), 7.39–7.44 (3H), 7.66 (1H, s).

SYNTHESIS EXAMPLE 8

Synthesis of 4-(2,4-dichlorobenzoyl)-1-methyl-5-(2-ethoxybenzyloxy)-pyrazole

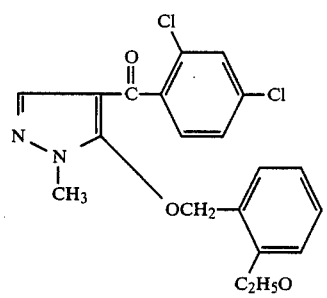

(Compound No. 2.8)

In 20 ml of N,N-dimethylformamide was dissolved 1.45 g (0.005 mol) of 4-(2,4-dichlorobenzoyl)-1-methyl-5-chloropyrazole. Then were added to the resulting solution 0.28 g (0.005 mol) of powdery potassium hydroxide and subsequently 0.76 g (0.005 mol) of 2-ethoxybenzylalcohol, and the resulting mixture was stirred at room temperature for 8 hours. After adding with water and ethyl acetate, the reaction mixture was shaked, and the organic layer was separated, washed with saturated brine and dried over anhydrous sodium sulfate. The solvent was distilled off therefrom under reduced pressure.

The resulting oil was purified through silica gel column chromatography using benzene as an eluant to give 1.45 g of the title compound (yield 75%).

$^1$H-NMR ($\delta$, ppm, CDCl$_3$): 1.35 (3H, t, J=7 Hz), 3.49 (3H, s), 4.43 (2H, q, J=7 Hz), 5.47 (2H, s), 6.75–7.45 (8H).

In the same manner as in Synthesis Examples 1, 2 and 6 through 8, the compounds listed in Table 3 were synthesized. The compounds obtained in Synthesis Examples 6 and 8 are also listed in Table 3.

TABLE 3

The compounds of the formula:

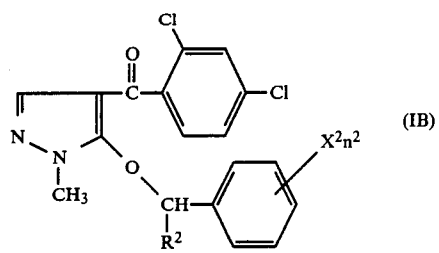

(IB)

| Compound No. | $-CH(R^2)-\text{C}_6\text{H}_{...}X^2_{n2}$ | Appearance or m.p. (°C.) | $^1$H-NMR (δ, ppm, CDCl$_3$) $>N-CH_3$ | $-O-CH(R^2)-\text{C}_6\text{H}_{...}X^2_{n2}$ | others |
|---|---|---|---|---|---|
| 2.1 | $-CH_2-\text{C}_6\text{H}_4-\text{BrCH}_2$ (o) | oil | 3.52 | 5.66 | 4.64(2H,s) |
| 2.2 | $-CH_2-\text{C}_6\text{H}_4-\text{CF}_3$ (o) | oil | 3.54 | 5.68 | — |
| 2.3 | $-CH_2-\text{C}_6\text{H}_4-\text{CF}_3$ (m) | oil | 3.58 | 5.63 | — |
| 2.4 | $-CH(CH_3)-\text{C}_6\text{H}_4-\text{OCH}_3$ (o) | oil | 3.45 | 1.57(3H,d,J=7Hz)<br>6.24(1H,q,J=7Hz) | 3.56(3H,s) |
| 2.5 | $-CH_2-\text{C}_6\text{H}_4-\text{CH}_3\text{O}$ (o) | oil | 3.46 | 5.46 | 3.76(3H,s) |
| 2.6 | $-CH_2-\text{C}_6\text{H}_4-\text{OCH}_3$ (p) | 83~89 | 3.45 | 5.44 | 3.78(3H,s) |
| 2.7 | $-CH_2-\text{C}_6\text{H}_2(\text{OCH}_3)_3$ | 95~98 | 3.53 | 5.44 | 3.80(9H,s) |
| 2.8 | $-CH_2-\text{C}_6\text{H}_4-\text{C}_2\text{H}_5\text{O}$ (o) | 120~122 | 3.49 | 5.47 | 1.35(3H,t,J=7Hz)<br>4.43(2H,q,J=7Hz) |
| 2.9 | $-CH_2-\text{C}_6\text{H}_4-\text{CHF}_2\text{O}$ (o) | oil | 3.53 | 5.54 | 6.55(1H,t,J=75Hz) |
| 2.10 | $-CH_2-\text{C}_6\text{H}_4-\text{CF}_2\text{CH}_2\text{O}$ (o) | oil | 3.52 | 5.52 | 4.37(2H,q,J=8Hz) |

TABLE 3-continued

The compounds of the formula:

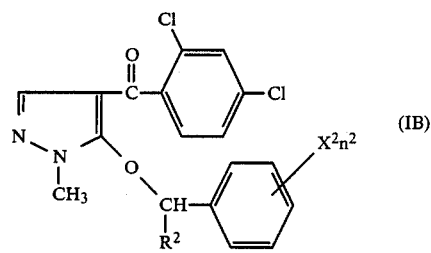
(IB)

| Compound No. | $-\underset{R^2}{\underset{|}{CH}}-\underset{}{\bigcirc}-X^2n^2$ | Appearance or m.p. (°C.) | $^1$H-NMR (δ, ppm, CDCl$_3$) | | |
|---|---|---|---|---|---|
| | | | $\underset{/}{\overset{\backslash}{N}}-C\underline{H}_3$ | $-O-\underset{\underline{R}^2}{\underset{|}{C\underline{H}}}-\bigcirc-X^2n^2$ | others |
| 2.11 | $-CH_2-\bigcirc-CH=CH_2$ (meta) | — | 3.52 | 5.53 | — |
| 2.12 | $-CH_2-\bigcirc-CH=CH_2$ (para) | — | 3.50 | 5.51 | — |
| 2.13 | $-CH_2-\bigcirc-\bigcirc$ | oil | 3.52 | 5.55 | — |
| 2.14 | $-CH_2-\bigcirc$ (NC ortho) | 87~91.5 | 3.67 | 5.74 | — |
| 2.15 | $-CH_2-\bigcirc-CN$ | 138~142 | 3.62 | 5.62 | — |
| 2.16 | $-CH_2-\bigcirc-O-\bigcirc$ | oil | 3.45 | 5.48 | — |
| 2.17 | $-CH_2-\bigcirc-COOC_2H_5$ | oil | 3.52 | 5.57 | 1.36(3H,t,J=7Hz) 4.33(2H,q,J=7Hz) |
| 2.18 | $-CH_2-\bigcirc-\overset{O}{\overset{\|}{C}}-CH_3$ | oil | 3.54 | 5.58 | 2.53(3H,s) |
| 2.19 | $-CH_2-\bigcirc$ (CH$_3$SO$_3$) | oil | 3.57 | 5.62 | 3.21(3H,s) |
| 2.20 | $-CH_2-\bigcirc-\underset{CH_3}{\underset{|}{C}}\overset{O-}{\underset{O-}{}}$ | oil | 3.51 | 5.51 | 1.62(3H,s) |

In accordance with the foregoing synthesis examples, the compounds listed in Table 4 may be readily synthesized.

TABLE 4
The compounds of the formula:
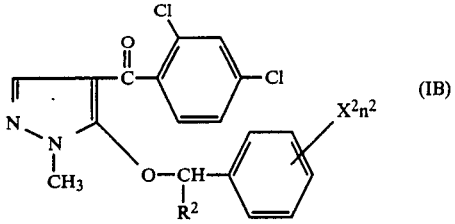
(IB)
| Compound No. | —CH(R²)—Ar(X²)ₙ₂ | Compound No. | —CH(R²)—Ar(X²)ₙ₂ |
|---|---|---|---|
| 2.21 | 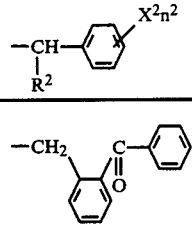 | 2.30 | 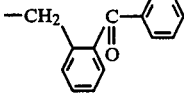 |
| 2.22 | 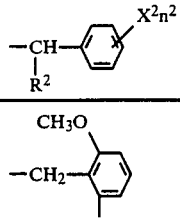 | 2.31 | 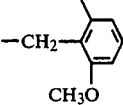 |
| 2.23 | 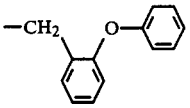 | 2.32 | 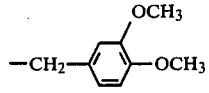 |
| 2.24 | 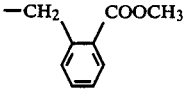 | 2.33 | 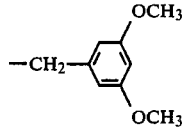 |
| 2.25 | 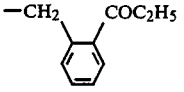 | 2.34 | 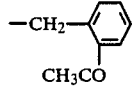 |
| 2.26 | 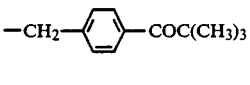 | 2.35 | 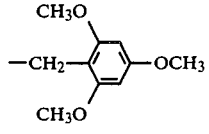 |
| 2.27 | 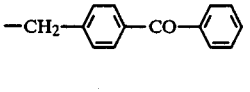 | 2.36 | 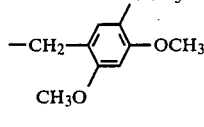 |
| 2.28 | 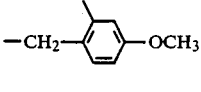 | 2.37 | 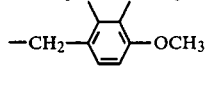 |
| 2.29 | 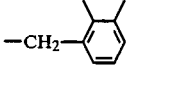 | 2.38 |  |

TABLE 4-continued

The compounds of the formula:

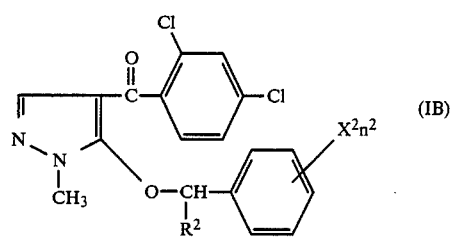

| Compound No. | —CH(R²)—C₆H₄—X²ₙ² | Compound No. | —CH(R²)—C₆H₄—X²ₙ² |
|---|---|---|---|
| 2.39 | —CH₂—C₆H₂(OC₂H₅)₃ (3,4,5-triethoxybenzyl) | 2.48 | —CH((CH₃)₂CH)—C₆H₄(o-COCH₃) |
| 2.40 | —CH(C₂H₅)—C₆H₄—OCH₃ | 2.49 | —CH(n-C₃H₇)—C₆H₄—COCH₃ |
| 2.41 | —CH(C₂H₅)—C₆H₄—COCH₃ | 2.50 | —CH((CH₃)₂CH)—C₆H₄—COCH₃ |
| 2.42 | —CH(C₂H₅)—C₆H₄(o-OCH₃) | 2.51 | —CH₂—C₆H₄—COCH₃ |
| 2.43 | —CH(C₂H₅)—C₆H₄(o-COCH₃) | 2.52 | —CH(C₂H₅)—C₆H₄(o-COOC₂H₅) |
| 2.44 | —CH(C₂H₅)—C₆H₄—C(CH₃)(OCH₂CH₂O) (4-(2-methyl-1,3-dioxolan-2-yl)) | 2.53 | —CH(C₂H₅)—C₆H₄(o-CN) |
| 2.45 | —CH((CH₃)₂CH)—C₆H₄—OCH₃ | 2.54 | —CH₂—C₆H₄(m-CH₂Br) |
| 2.46 | —CH(n-C₃H₇)—C₆H₄(o-OCH₃) | 2.55 | —CH₂—C₆H₄(o-CH₂Cl) |
| 2.47 | —CH(n-C₃H₇)—C₆H₄(o-COCH₃) | 2.56 | —CH₂—C₆H₄—CH₂Cl |
| 2.57 | —CH₂—C₆H₄—CH₂Br | 2.65 | —CH₂—C₆H₃(2-CH₂Br)(5-OCH₃) |

TABLE 4-continued

The compounds of the formula:

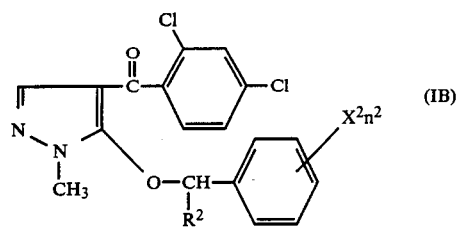

| Compound No. | $-\underset{R^2}{\underset{|}{CH}}-\text{Ar}X^2n^2$ | Compound No. | $-\underset{R^2}{\underset{|}{CH}}-\text{Ar}X^2n^2$ |
|---|---|---|---|
| 2.58 | −CH₂−C₆H₃(COCH₃)(CH₃O) | 2.66 | −CH₂−C₆H₃(OCH₃)(BrCH₂) |
| 2.59 | −CH₂−C₆H₃(CH₃O)(COCH₃) | 2.67 | −CH₂−C₆H₃(OCH₃)(COOC₃H₇−n) |
| 2.60 | −CH₂−C₆H₃(COOC₂H₅)(CH₃O) | 2.68 | −CH₂−C₆H₃(CH₃O)(CH₂Cl) |
| 2.61 | −CH₂−C₆H₃(CH₃O)(COOC₂H₅) | 2.69 | CH₂−C₆H₃(OCH₃)(CH₂Cl) |
| 2.62 | −CH₂−C₆H₃(OCHF₂)(OCHF₂) | 2.70 | −CH₂−C₆H₄−C(CH₃)=CH₂ |
| 2.63 | −CH₂−C₆H₃(CF₂HO)(OCHF₂) | 2.71 | −CH₂−C₆H₄−CH₂CH=CH₂ |
| 2.64 | −CH₂−C₆H₃(CF₂HO)(OCHF₂) | 2.72 | −CH₂−C₆H₄−CH=CH₂ |

SYNTHESIS EXAMPLE 9

Synthesis of
4-(2,4-dichloro-3-methylbenzoyl)-1-methyl-5-hydroxypyrazole

After 13.5 g (0.1 mol) of 1-methyl-5-hydroxypyrazole hydrochloride was dissolved into 20% aqueous solution containing 11.2 g (0.2 mol) of potassium hydroxide at 0° C., 50 ml of chloroform was added thereto to obtain a two layer system. Thereafter, 22.4 g (0.1 mol) of 2,4-dichloro-3-methylbenzoylchloride was added dropwise to it, and the reaction was carried out at room temperature for 2 hours. The chloroform layer was separated from the reaction solution, and dried. Chloroform was then distilled off under reduced pressure to obtain a solid product. To the resulting solid product was added 25 ml of 1,4-dioxane and 27.6 g (0.2 mol) of potassium carbonate, and heated up to 100°–120° C.

After one hour at which precipitates were formed, the solvent was distilled off. Then, 30 ml of isopropyl alcohol was added to the residue, and the solution was refluxed for 30 min. The resulting powdery product was poured into ice water and dissolved in it. The solution was acidified with hydrochloric acid to produce a solid product, which was filtered and dried. It was then recrystallized from 95% ethanol to obtain 20.2 g of the title compound (yield: 71%).

m.p.: 131.0°–135.0° C.

$^1$H-NMR (CDCl$_3$, δ, ppm): 2.50 (3H, s), 3.66 (3H, s), 7.07–7.42 (3H), 9.58 (1H, s).

SYNTHESIS EXAMPLE 10

Synthesis of 7-chloro-1-methyl-[1]-benzopyrano[2,3-c]pyrazol-4-on 1.38 g (0.01 mol) of potassium carbonate was added to 2.71 g (0.01 mol) of 4-(2,4-dichlorobenzoyl)-1-methyl-5-hydroxypyrazole dissolved in 20 ml of N,N-dimethylformamide, and the reaction mixture was stirred at 100°–120° C. for 5 hours. After cooling, the reaction mixture was poured into ice water, and extracted with chloroform. The chloroform layer was dried and the solvent was distilled off under reduced pressure to obtain a solid product. It was recrystallized from methanol to obtain 2.15 g of the title compound as colorless needle crystals (yield: 92%).

m.p.: 193°–198° C.

SYNTHESIS EXAMPLE 11

Synthesis of 4-(2-ethoxy-4-chlorobenzoyl)-1-methyl-5-hydroxypyrazole 2.35 g (0.01 mol) of 1-chloro-1-methyl-[1]benzopyrano[2,3-c]pyrazole-4-on was added to 0.4 g (0.01 mol) of sodium hydroxide dissolved in 20 ml of absolute ethanol, and the reaction mixture was refluxed for 3 hours. After cooling, the reaction mixture was poured into ice water and acidified with hydrochloric acid, and then extracted with chloroform. After drying, the solvent was distilled off under reduced pressure to obtain 2.1 g of the title compound (yield: 75%).

$^1$H-NMR(CDCl$_3$, δ, ppm): 1.35 (3H, t, J=7 Hz), 3.69 (3H, s), 4.28 (2H, q, J=7 Hz), 6.84–7.72 (4H), 12.18 (1H, s).

SYNTHESIS EXAMPLE 12

Synthesis of 4-(2,4-dichloro-3-methylbenzoyl)-1-methyl-5-benzyloxypyrazole (Compound No. 3.3)

1.43 g (0.005 mol) of 4-(2,4-dichloro-3-methylbenzoyl)-1-methyl-5-hydroxypyrazole was dissolved in 20 ml of benzene containing 0.50 g (0.005 mol) of triethylamine, and 0.86 g (0.005 mol) of benzylbromide was added thereto. Then, the reaction mixture was refluxed with stirring for 2 hours. After cooling, the precipitated salt was filtered off, and benzene was distilled off from the residual solution under reduced pressure. The resulting oily product was purified through a silica gel column chromatography (eluent:benzene) to obtain 1.67 g of the title compound (yield 89%).

$n_D^{20}=1.6175$ $^1$H-NMR(CDCl$_3$, δ, ppm): 2.46 (3H, s), 3.45 (3H, s), 5.52 (2H, s), 7.02–7.39 (8H).

The following compounds shown in Table 5 according to the present invention were synthesized in the manner simmilar to in Synthesis Examples 1 and 9–12.

TABLE 5 (IC)

| Compound No. | $Y^3m^3$ (aryl) | $-CH(R^3)-$ aryl $X^3n^3$ | Appearance or m.p. (°C.) or $[α]_D$ | $N-CH_3$ | $-O-CH(R^3)-$ aryl $X^3n^3$ | others |
|---|---|---|---|---|---|---|
| 3.1 | $O_2N$, Cl | $-CH_2-$Ph | 147~148 | 3.42 | 5.47 | — |
| 3.2 | Cl, $NO_2$ | $-CH_2-$Ph | $n_D^{20}=1.6143$ | 3.49 | 5.53 | — |
| 3.3 | Cl, $CH_3$, Cl | $-CH_2-$Ph | $n_D^{20}=1.6175$ | 3.45 | 5.52 | 2.46(3H,s) |
| 3.4 | Cl, $CH_3$, Cl | $-CH_2-$Ph($CH_3$) | $n_D^{20}=1.6159$ | 3.42 | 5.54 | 2.41(3H,s) 2.46(3H,s) |

TABLE 5-continued (IC)
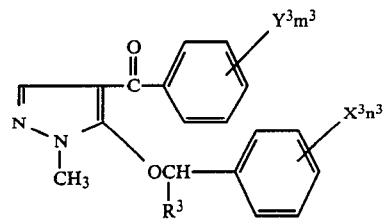

| Compound No. | Y³m³ (aryl) | X³n³ / R³ group | Appearance or m.p. (°C.) OR [α]_D | ¹H-NMR(δ,ppm,CDCl₃) N-CH₃ | -O-CH(R³)- | others |
|---|---|---|---|---|---|---|
| 3.5 | 2,4-Cl, 3-CH₃ phenyl | -CH₂-(2-Cl-phenyl) | oil | 3.56 | 5.64 | 2.49(3H,s) |
| 3.6 | 2-O₂N, 4-CH₃ phenyl | -CH₂-phenyl | $n_D^{20} = 1.6001$ | 3.38 | 5.48 | 2.38(3H,s) |
| 3.7 | 2,4-Cl, 3-CH₃ phenyl | -CH₂-(2-CF₃-phenyl) | oil | 3.54 | 5.61 | 2.46(3H,s) |
| 3.8 | 2,4-Cl, 3-CH₃ phenyl | -CH₂-(4-Br-phenyl) | 89.0~91.0 | 3.52 | 5.50 | 2.49(3H,s) |
| 3.9 | 2-phenyl-phenyl | -CH₂-phenyl | oil | 3.30 | 5.32 | — |
| 3.10 | 3,4-(OCH₃)₂ phenyl | -CH₂-phenyl | oil | 3.52 | 5.32 | 3.89(6H,s) |
| 3.11 | 2-C₂H₅O, 4-Cl phenyl | -CH₂-phenyl | oil | 3.59 | 4.99 | 1.23(3H,t, J = 7Hz) 4.34(2H,q, J = 7Hz) |
| 3.12 | 2,4-Cl, 3-CH₃ phenyl | -CH₂-(2-CHF₂O-phenyl) | oil | 3.56 | 5.57 | 2.49(3H,s) 6.55(1H,t, J = 74Hz) |
| 3.13 | 2,4-Cl, 3-CH₃ phenyl | -CH₂-(2-O₂N-phenyl) | 136~140 | 3.65 | 5.86 | 2.45(3H,s) |
| 3.14 | 2,4-Cl, 3-CH₃ phenyl | -CH₂-(3-CH=CH₂-phenyl) | — | 3.53 | 5.56 | 2.52(3H,s) |
| 3.15 | 2,4-Cl, 3-CH₃ phenyl | -CH₂-(4-CH=CH₂-phenyl) | — | 3.51 | 5.54 | 2.52(3H,s) |

TABLE 5-continued (IC) structure with Y³m³, X³n³, OCH/R³, N-N-CH₃, pyrazole-C(=O)-phenyl

| No. | Ar (Y³m³) | -CH(R³)- group | form | (col) | (col) | NMR |
|---|---|---|---|---|---|---|
| 3.16 | 2,6-Cl₂-3-CH₃-phenyl | -CH(CH₃)-phenyl | oil | 3.41 | 1.73(3H,d, J=7Hz) 6.12(1H,q, J=7Hz) | 2.46(3H,s) |
| 3.17 | 2-CF₃-phenyl | -CH₂-phenyl | oil | 3.45 | 5.52 | — |
| 3.18 | 2,6-Cl₂-3-CH₃-phenyl | -CH₂-(3,4,5-tri-OCH₃-phenyl) | oil | 3.51 | 5.44 | 2.49(3H,s) 3.80(9H,s) 6.58(2H,s) |

The compounds shown in Table 6 according to the present invention may be readily synthesized in the similar manner as in the preceding Synthesis Examples.

TABLE 6

(IC) structure

| Compound No. | Y³m³-aryl | -CH(R³)-aryl (X³n³) |
|---|---|---|
| 3.19 | 2-O₂N-4-Cl-phenyl | -CH₂-(2-CH₃-phenyl) |
| 3.20 | 2-O₂N-4-Cl-phenyl | -CH₂-(4-CH₃-phenyl) |
| 3.21 | 2-O₂N-4-Cl-phenyl | -CH(CH₃)-phenyl |
| 3.22 | 2-O₂N-4-Cl-phenyl | -CH(CH₃)-(4-Cl-phenyl) |
| 3.23 | 2-Cl-4-CF₃-phenyl | -CH₂-phenyl |

TABLE 6-continued

| Compound No. | Y³m³-aryl | -CH(R³)-aryl (X³n³) |
|---|---|---|
| 3.24 | 2-Cl-4-CF₃-phenyl | -CH₂-(2-CH₃-phenyl) |
| 3.25 | 2-Cl-4-CF₃-phenyl | -CH₂-(4-CH₃-phenyl) |
| 3.26 | 2-Cl-4-CF₃-phenyl | -CH₂-(2-Cl-phenyl) |
| 3.27 | 2-Cl-4-CF₃-phenyl | -CH₂-(4-Cl-phenyl) |
| 3.28 | 2-Cl-4-CF₃-phenyl | -CH₂-(2,4-Cl₂-phenyl) |
| 3.29 | 2-Cl-4-CF₃-phenyl | -CH₂-(3-CF₃-phenyl) |

TABLE 6-continued

General structure (IC):

Pyrazole with N-CH₃, bearing -C(=O)-C₆H₄-Y³ₘ₃ and -OCH(R³)-C₆H₄-X³ₙ₃ substituents.

| Compound No. | Y³ₘ₃ (aryl) | -CH(R³)-aryl-X³ₙ₃ |
|---|---|---|
| 3.30 | 3-Cl, 4-CF₃-phenyl | -CH₂-(3-CH=CH₂-phenyl) |
| 3.31 | 3-Cl, 4-CF₃-phenyl | -CH(CH₃)-phenyl |
| 3.32 | 3-Cl, 4-CF₃-phenyl | -CH(CH₃)-(4-Cl-phenyl) |
| 3.33 | 2-CH₃, 3-Cl, 4-Cl-phenyl | -CH₂-(2,4-diCl-phenyl) |
| 3.34 | 2-CH₃, 3-Cl, 4-Cl-phenyl | -CH₂-(2,6-diF-phenyl) |
| 3.35 | 2-CH₃, 3-Cl, 4-Cl-phenyl | -CH(CH₃)-(2-Cl-phenyl) |
| 3.36 | 2-CH₃, 3-Cl, 4-Cl-phenyl | -CH(CH₃)-(2-CH₃-phenyl) |
| 3.37 | 2-CH₃, 3-Cl, 4-Cl-phenyl | -CH₂-(2-Br-phenyl) |
| 3.38 | 2-O₂N, 4-Cl-phenyl | -CH₂-(2,4-diCl-phenyl) |
| 3.39 | 2-O₂N, 4-Cl-phenyl | -CH₂-(2-Cl, 6-F-phenyl) |
| 3.40 | 2-O₂N, 4-Cl-phenyl | -CH₂-(2,6-diF-phenyl) |
| 3.41 | 2-O₂N, 4-Cl-phenyl | -CH(C₂H₅)-phenyl |
| 3.42 | 2-O₂N, 4-Cl-phenyl | -CH₂-(3-CF₃-phenyl) |
| 3.43 | 2-O₂N, 4-Cl-phenyl | -CH₂-(3-CH=CH₂-phenyl) |
| 3.44 | 2-O₂N, 4-Cl-phenyl | -CH₂-(4-CH=CH₂-phenyl) |
| 3.45 | 2-Cl, 4-NO₂-phenyl | -CH₂-(2-CH₃-phenyl) |
| 3.46 | 2-Cl, 4-NO₂-phenyl | -CH₂-(3-CH₃-phenyl) |
| 3.47 | 2-Cl, 4-NO₂-phenyl | -CH₂-(4-CH₃-phenyl) |
| 3.48 | 2-O₂N, 4-Cl-phenyl | -CH₂-(2,3-diCl-phenyl) |
| 3.49 | 3-Cl, 4-CF₃-phenyl | -CH₂-(2-F-phenyl) |
| 3.50 | 3-Cl, 4-CF₃-phenyl | -CH₂-(2,3-diF-phenyl) |

TABLE 6-continued $$\text{(IC)}$$

Structure: pyrazole with N-CH₃, connected to C(=O)-phenyl(Y³ₘ³) and O-CH(R³)-phenyl(X³ₙ³)

| Compound No. | —phenyl-Y³ₘ³ | —CH(R³)-phenyl-X³ₙ³ |
|---|---|---|
| 3.51 | 2-O₂N, 5-Cl phenyl | —CH₂—(3-CH₃-phenyl) |
| 3.52 | 2-Cl, 4-CF₃ phenyl | —CH₂—(2,6-diCl-phenyl) |
| 3.53 | 2-Cl, 4-CF₃ phenyl | —CH(CH₃)—(2-Cl-phenyl) |
| 3.54 | 2-Cl, 3-CH₃, 4-Cl phenyl | —CH₂—(2,6-diCl-phenyl) |
| 3.55 | 2-O₂N, 5-Cl phenyl | —CH₂—(2-Cl-phenyl) |
| 3.56 | 2-Cl, 3-CH₃, 4-Cl phenyl | —CH₂—(2-CH₃, 4-CH₃-phenyl) |
| 3.57 | 2-O₂N, 5-Cl phenyl | —CH(CH₃)—(2-Cl-phenyl) |
| 3.58 | 2-Cl, 3-CH₃, 4-Cl phenyl | —CH(C₂H₅)—phenyl |
| 3.59 | 2-Cl, 4-NO₂ phenyl | —CH₂—(2-Cl-phenyl) |
| 3.60 | 2-Cl, 4-NO₂ phenyl | —CH₂—(3-Cl-phenyl) |
| 3.61 | 2-Cl, 4-NO₂ phenyl | —CH₂—(4-Cl-phenyl) |
| 3.62 | 2-Cl, 4-NO₂ phenyl | —CH₂—(2,4-diCl-phenyl) |
| 3.63 | 2-Cl, 3-CH₃, 4-Cl phenyl | —CH(CH₃)—(4-Cl-phenyl) |
| 3.64 | 2-O₂N-phenyl | —CH₂—phenyl |
| 3.65 | 2-O₂N-phenyl | —CH₂—(3-CH₃-phenyl) |
| 3.66 | 2-O₂N-phenyl | —CH₂—(4-CH₃-phenyl) |
| 3.67 | 2-O₂N-phenyl | —CH₂—(2-Cl-phenyl) |
| 3.68 | 2-O₂N-phenyl | —CH₂—(4-Cl-phenyl) |
| 3.69 | 2-O₂N-phenyl | —CH₂—(2,4-diCl-phenyl) |
| 3.70 | 2-O₂N-phenyl | —CH(CH₃)—phenyl |
| 3.71 | 2-Cl, 3-CH₃, 4-Cl phenyl | —CH₂—(2-BrCH₂-phenyl) |
| 3.72 | 2-Cl, 3-CH₃, 4-Cl phenyl | —CH₂—(3-CH₂Cl-phenyl) |
| 3.73 | 2-O₂N, 5-Cl phenyl | —CH₂—(4-CH₂Br-phenyl) |

TABLE 6-continued (IC)

Structure: pyrazole with N-N-CH3, C=O to phenyl(Y³m³), OCH(R³)-phenyl(X³n³)

| Compound No. | (Y³m³ aryl) | -CH(R³)-(X³n³ aryl) |
|---|---|---|
| 3.74 | O₂N-phenyl-Cl | -CH₂-phenyl(BrCH₂) |
| 3.75 | Cl,CF₃-phenyl | -CH₂-phenyl-CH₂Cl |
| 3.76 | Cl,CF₃-phenyl | -CH₂-phenyl(CF₂BrO) |
| 3.77 | F₃C,Cl-phenyl | -CH₂-phenyl |
| 3.78 | F₃C,Cl-phenyl | -CH₂-phenyl(Cl) |
| 3.79 | F₃C,Cl-phenyl | -CH₂-phenyl-Cl |
| 3.80 | F₃C,Cl-phenyl | -CH₂-phenyl(CH₃) |
| 3.81 | F₃C,Cl-phenyl | -CH₂-phenyl-CH₃ |
| 3.82 | F₃C,Cl-phenyl | -CH₂-phenyl(Cl,Cl) |
| 3.83 | F₃C,Cl-phenyl | -CH(CH₃)-phenyl |
| 3.84 | F₃C,Cl-phenyl | -CH₂-phenyl(Cl,Cl) |
| 3.85 | O₂N-phenyl-Cl | -CH₂-phenyl(CF₃CH₂O, CF₃CH₂O) |
| 3.86 | O₂N-phenyl-Cl | -CH₂-phenyl(OCF₃) |
| 3.87 | Cl,CH₃,Cl-phenyl | -CH₂-phenyl(OCH₂CF₃) |
| 3.88 | Cl,CH₃,Cl-phenyl | -CH₂-phenyl(CF₃CH₂O, CH₃) |
| 3.89 | Cl,CF₃-phenyl | -CH₂-phenyl(CF₂BrO, CH₂Br) |
| 3.90 | Cl,CF₃-phenyl | -CH(CH₃)-phenyl(OCH₂CF₃) |

SYNTHESIS EXAMPLE 13

Synthesis of 4-(2,4-dichlorobenzoyl)-1-methyl-5-(2-chlorobenzyloxy)-pyrazole

To a mixture of 1.33 g (0.0049 mol) of 4-(2,4-dichlorobenzoyl)-1-methyl-5-hydroxypyrazole, 0.54 g (0.0054 mol) of triethylamine and 30 ml of toluene was added 1.3 g (0.0059 mol) of o-chlorobenzyl methanesulfonate. Then, the reaction mixture was refluxed with stirring for 2 hours. After cooling, the reaction mixture was washed with 20 ml of water three times, and the organic layer was separated. After drying over anhydrous sodium sulfate, the organic layer was concentrated under reduced pressure and was subjected to a column chromatography (silica gel, eluent; ethyl acetate:benzene=1:9) to obtain 1.5 g of the title compound (yield: 77%).

SYNTHESIS EXAMPLE 14

Synthesis of 4-(2,4-dichlorobenzoyl)-1-methyl-5-(2-chlorobenzyloxy)-pyrazol

Using 1.75 g (0.059 mol) of o-chlorobenzyltocylate instead of 1.3 g of o-chlorobenzyl methanesulfonate in Example 13, the refluxing was carried out under heating for 4 hours. The reaction mixture was treated in a manner similar to the steps in Synthesis Example 13 to obtain 1.2 g of the title compound (yield 62%).

The compounds of the formula I according to the present invention may be employed as an active ingredient of selective herbicides, especially in the field of paddy rice. The compounds of the invention are active not only against broad spectrum of annual weeds but are also particularly effective in powerfully controlling and damaging perennial weeds such as bulrush species (Scirpus hotarui, Scirpus fluviatilis, etc.), perennial flat sedge species (Cyperus serotinus, etc.), arrowhead (Sagittaria pygmaea, etc.), perennial spikerush species (Eleocharis kuroguwai, Fleocharis acicularis, etc.) which exhibit resistance against the conventional herbicides and are difficult to control thereby.

The application processes, such as spraying, atomising, dusting, scattering, brushing or pouring, and likewise the type of composition, are selected to suit the objectives to be achieved and the given conditions.

The weeds against which the compounds according to the present invention are applicable are shown below. These are merely illustrative of the present invention, but they are not to be interpreted to restrict the scope of the present invention. Weeds against which the present invention are effective include: bulrush species (Scirpus hotarui, Scirpus fluviatilis), flat sedge species (Cyperus serotinus, Cyperus articulatus, Cyperus microiria), nut sedge species (Cyperus esculantus), arrowhead species (Sagitaria pygmea), spikerush species (Eleocharis acicularis, Eleocharis kuroguwai), pondweed species (Potamogeton nodosus), water plantain species (Alisma gramineum), duck salad species (Monochoria vaginalis), false pimpernel species (Lindernia procubens), tooth cup species (Rotala indica), barnyardgrass species (Echinochloa crus-galli), water purslane species (Ludwigia palustris), waterwort species (Elatine americana), waterstarwort species (Callitriche verna), sprangletop species (Leptochloa uninervia), beggerticks species (Bidens frondosa), alligatorweed species (Alternanthera philoxeroides), vetch species (Vicia sativa), hemp sesbania species (Sesbania exaltata).

The herbicidal compositions containing as an active ingredient compounds according to the present invention are applicable to non-cultivation lands such athletic fields, vacant lands, railroad side sites, for the purpose of damaging or destroying and controlling a variety of the weeds in addition to the agricultural and horticultural lands such as farmlands, paddy fields, fruit gardens, etc. The application dosage of the compounds according to the present invention may be varied deponding upon the places where the herbicidal composition is to be applied, application seasons or time, application methods, kinds of intended weeds, crops or foods to be cultivated, etc., but it may generally range from 0.025 to 10 kg/ha, preferably from 0.05 to 5.0 kg/ha.

Within the practical application dosage of each compound according to the present invention, the compound will have substantially no phytotoxicity toward cultivated products such as rice plants, corn plants, cotton, wheat, etc.

The compounds according to the present invention which are thought to be most preferable as the active ingredient of a herbicidal composition are ones having the preferred substituents (for instance A, X, Y, etc.) described in connection with the formulae (I), (IA), (IB), and (IC).

When applied as herbicidal compositions, the compounds according to the present invention may be applied together with an appropriate carrier. The compounds of the invention may be marketed in appropriate formulations such as emulsifiable concentrate, wettable powder, dust, granule, etc., by adding thereto auxiliary agents such as emulsifier, dispersing agent, suspending agent, penetrating agent, spreader, stabilizer etc. When necessary, it may be admixed with other kinds of herbicides, a variety of insecticides, germicides, synergists, fertilizers, antifoam agents, viscosity regulators, binders, adhesives, etc. when formulated or practically applied. As the other kinds of herbicides as mentioned above, there may be included those as described in Farm Chemicals Handbook, 69th edition (1983).

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface active reagent (surfactant).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite, bentonite diatomaceous earth, or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pre-granulated materials of inorganic or organic nature, such as in particular dolomite or ground plant.

The herbicidal compositions can be applied to the locus or to the area which is to be protected from weeds in the form of a spray, a powder, dust or granule. The composition may be directly applied to the locus or to the area which is already infested with weeds. The compositions may thus be applied to the leaves or to the soil surface in the form of a spray. On the other hand, the dry compositions in granular form may be scattered on to the soil surface of paddy field.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of high fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ringwood, N.J., 1980, and Sisely and Wood, "Encyclopedia of Surface Active Agents", Chemical Publishing Co., Inc. New York, 1980.

The herbicidal compositions contain as a rule 0.1 to 99%, particularly 0.1 to 95%, of active ingredient of the formula I, 99.9 to 1%, especially 99.9 to 5%, of a solid or liquid additive, and 0 to 25%, in particular 0.1 to 25%, of a tenside. Whereas commercial products are preferably in the form of concentrated compositions, the compositions employed by the end-user are as a rule diluted.

The specific formulations of the compounds according to the present invention are described below. "Part" means "parts by weight" in the following. The formulations are merely illustrative of the present invention, but they are not to be interpreted to restrict the scope of the invention.

| Formulation 1: Granules | |
|---|---|
| Compound No. 1.1, 2.1 or 3.1 of the invention (active ingredient) | 5 parts |
| bentonite | 55 parts |
| talc | 40 parts |

After the above ingredients were homogeneously crushed and blended with one another, a small amount of water was added thereto. Then, the mixture was kneaded well, and granulated by means of an extrusion type granulator. The granulated product was dried to obtain granules. Application is done at the ratio of 0.025 to 10 kg/ha, preferably, 0.05 to 5 kg/ha of the active ingredient.

| Formulation 2: Wettable powders | |
|---|---|
| Compound No. 1.4, 2.4 or 3.4 of the invention (active ingredient) | 50 parts |
| Zeeklite A (kaolin type clay: trade name supplied by Ziecleid Industries, Co.) | 46 parts |
| Sorpol 5039 (mixture of non-ion type surface active agent and anion type surface active agent: trade name supplied by Toho Chemical Co., Ltd., Japan) | 2 parts |
| Carplex (congelation inhibitor) (white carbon: trade name supplied by Shionogi Pharmaceutical Co., Ltd., Japan) | 2 parts |

The above ingredients were homogeneously crushed and blended with one another to obtain wettable powders. When in use, they are diluted with water to 50th–1,000th concentration, and it is applied at the ratio of 0.025–10 kg/ha, preferably 0.05 to 5.0 kg/ha of the active ingredient.

| Formulation 3: Emulsifiable concentrate | |
|---|---|
| Compound No. 1.1 or 1.20 of the invention (active ingredient) | 30 parts |
| xylene | 55 parts |
| methylnaphthalene | 10 parts |
| Sorpol 2680 (mixture of non-ionic type surface active agent and anion type surface active agent: trade name supplied by Toho Chemical Co., Ltd.) | 5 parts |

The above ingredients are homogeneously blended with one another to obtain an emulsifiable concentrate. When in use, it is diluted with water to 50–1,000th concentration or it is applied as it is without being diluted to the water surface of paddy field. Application is done at the ratio of 0.025–10 kg/ha, preferably, 0.05 to 5.0 kg/ha of the active ingredient.

Next, the herbicidal activity of the compounds according to the present invention will be specifically described in connection with the following examples.

Biological Examples

Test example 1: Herbicidal effect test (1) in submerged conditions

After a certain amount of alluvial soil was placed in a Neubauer pot of 1/10,000 are (a), water was added thereto to obtain a submerged state of 2 cm in water depth through well-mixing. Seeds of barnyardgrass (*Echinochloa crus-galli*), ducksalad (*Monochoria vaginalis*), false pimpernel (*Lindernia procumbens*), toothcup (*Rotala indica*), bulrush (*Scirpus hotarui*) were mixedly sowed in the above pot, and tubers of arrowhead (*Sagittaria pygmaea*), perennial flate sedge (*Cyperus serotinus*), perennial spikerush (*Eleocharis kuroguwai*) were planted. The next day of the plantation, a predetermined amount of a diluted solution of the compound according to the present invention was added dropwise over the surface of the water in the pot by means of a measuring pipette.

Three weeks after the application, the herbicidal effect against the planted weeds was evaluated in the following standard of judgement:

| Evaluation Standard | |
|---|---|
| 5 | herbicidal rate above 90% (completely withered) |
| 4 | herbicidal rate 70–90% |
| 3 | herbicidal rate 40–70% |
| 2 | herbicidal rate 20–40% |
| 1 | herbicidal rate 5–20% |
| 0 | herbicidal rate below 5% (practically no efficacy) |

The above herbicidal rate was calculated by the following equation based on the weight measured of the live plants above soil in the herbicide-treated and the untreated plot:

$$\text{Herbicidal rate (\%)} = \left(1 - \frac{\text{weight of live plant above soil in herbicide - treated plot}}{\text{weight of live plant above soil in herbicide - untreated plot}}\right) \times 100$$

The results are shown in Table 7.

TABLE 7

| Compound No. | Application dosage (Kg/ha) | Annual weed | | | | Perennial weed | | | |
|---|---|---|---|---|---|---|---|---|---|
| | | barnyardgrass (*Echinochloa crus-galli*) | ducksalad (*Monochoria vaginalis*) | false pimpernel (*Lindernia procumbens*) | toothcup (*Rotala indica*) | bulrush (*Scirpus hotarui*) | arrowhead (*Sagittaria pygmaea*) | perennial flat sedge (*Cyperus serotinus*) | perennial spikerush (*Eleocharis kuroguwai*) |
| 1.1 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.2 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.3 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.4 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.5 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.6 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.9 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.14 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.15 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.16 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.20 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.27 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.50 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 1.55 | 0.5 | 5 | 5 | 5 | 5 | 5 | 5 | 5 | 5 |
| | 0.25 | 5 | 5 | 5 | 5 | 5 | 5 | 5 | 5 |
| | 0.125 | 5 | 5 | 5 | 5 | 5 | 5 | 5 | 5 |
| 2.1 | 1.0 | 5 | 5 | 5 | 5 | 5 | 5 | 5 | 5 |
| | 0.5 | 4 | 5 | 5 | 5 | 4 | 4 | 5 | 5 |
| 2.2 | 1.0 | 5 | 5 | 5 | 5 | 5 | 5 | 5 | 5 |

TABLE 7-continued

| | | Annual weed | | | | Perennial weed | | perennial | perennial |
|---|---|---|---|---|---|---|---|---|---|
| Compound No. | Application dosage (Kg/ha) | barnyardgrass (Echinochloa crus-galli) | ducksalad (Monochoria vaginalis) | false pimpernel (Lindernia procumbens) | toothcup (Rotala indica) | bulrush (Scirpus hotarui) | arrowhead (Sagittaria pygmaea) | flat sedge (Cyperus serotinus) | spikerush (Eleocharis kuroguwai) |
| 2.3 | 0.5 | 5 | 5 | 5 | 5 | 5 | 5 | 5 | 5 |
| | 1.0 | 5 | 5 | 5 | 5 | 5 | 5 | 5 | 5 |
| 2.4 | 0.5 | 5 | 5 | 5 | 5 | 5 | 4 | 5 | 5 |
| | 1.0 | 5 | 5 | 5 | 5 | 5 | 5 | 5 | 5 |
| 2.5 | 0.5 | 5 | 5 | 5 | 5 | 5 | 5 | 5 | 5 |
| | 1.0 | 5 | 5 | 5 | 5 | 5 | 5 | 5 | 5 |
| 2.6 | 0.5 | 5 | 5 | 5 | 5 | 5 | 5 | 5 | 5 |
| | 1.0 | 5 | 5 | 5 | 5 | 5 | 5 | 5 | 5 |
| 2.7 | 0.5 | 4 | 5 | 5 | 5 | 5 | 5 | 5 | 5 |
| | 1.0 | 5 | 5 | 5 | 5 | 5 | 5 | 5 | 5 |
| 2.8 | 0.5 | 5 | 5 | 5 | 5 | 5 | 5 | 5 | 5 |
| | 1.0 | 5 | 5 | 5 | 5 | 5 | 5 | 5 | 5 |
| 2.9 | 0.5 | 5 | 5 | 5 | 5 | 5 | 5 | 5 | 5 |
| | 1.0 | 5 | 5 | 5 | 5 | 5 | 5 | 5 | 5 |
| 2.10 | 0.5 | 5 | 5 | 5 | 5 | 5 | 5 | 5 | 5 |
| | 1.0 | 5 | 5 | 5 | 5 | 5 | 5 | 5 | 5 |
| 2.11 | 0.5 | 5 | 5 | 5 | 5 | 5 | 5 | 5 | 5 |
| | 1.0 | 5 | 5 | 5 | 5 | 5 | 5 | 5 | 5 |
| 2.13 | 0.5 | 5 | 5 | 5 | 5 | 5 | 5 | 5 | 5 |
| | 1.0 | 5 | 5 | 5 | 5 | 5 | 5 | 5 | 5 |
| 2.14 | 0.5 | 5 | 5 | 5 | 5 | 5 | 5 | 5 | 5 |
| | 1.0 | 5 | 5 | 5 | 5 | 5 | 5 | 5 | 5 |
| 2.15 | 0.5 | 5 | 5 | 5 | 5 | 5 | 5 | 5 | 5 |
| | 1.0 | 5 | 5 | 5 | 5 | 5 | 5 | 5 | 5 |
| 2.16 | 0.5 | 5 | 5 | 5 | 5 | 5 | 4 | 5 | 5 |
| | 1.0 | 5 | 5 | 5 | 5 | 5 | 5 | 5 | 5 |
| 2.17 | 0.5 | 5 | 5 | 5 | 5 | 5 | 5 | 5 | 5 |
| | 1.0 | 5 | 5 | 5 | 5 | 5 | 5 | 5 | 5 |
| 2.18 | 0.5 | 5 | 5 | 5 | 5 | 5 | 5 | 5 | 5 |
| | 1.0 | 5 | 5 | 5 | 5 | 5 | 5 | 5 | 5 |
| 2.19 | 0.5 | 4 | 5 | 5 | 5 | 5 | 5 | 5 | 5 |
| | 1.0 | 5 | 5 | 5 | 5 | 5 | 5 | 5 | 5 |
| 2.20 | 0.5 | 5 | 5 | 5 | 5 | 5 | 5 | 5 | 5 |
| | 1.0 | 5 | 5 | 5 | 5 | 5 | 5 | 5 | 5 |
| 3.1 | 0.25 | 5 | 5 | 5 | 5 | 5 | 5 | 5 | 5 |
| | 0.5 | 5 | 5 | 5 | 5 | 5 | 5 | 5 | 5 |
| 3.2 | 0.25 | 5 | 5 | 5 | 5 | 5 | 5 | 5 | 5 |
| | 0.5 | 5 | 5 | 5 | 5 | 5 | 5 | 5 | 5 |
| 3.3 | 0.25 | 5 | 5 | 5 | 5 | 5 | 5 | 5 | 5 |
| | 0.5 | 5 | 5 | 5 | 5 | 5 | 5 | 5 | 5 |
| 3.4 | 0.25 | 5 | 5 | 5 | 5 | 5 | 5 | 5 | 5 |
| | 0.5 | 5 | 5 | 5 | 5 | 5 | 5 | 5 | 5 |
| 3.5 | 0.25 | 5 | 5 | 5 | 5 | 5 | 5 | 5 | 5 |
| | 0.5 | 5 | 5 | 5 | 5 | 5 | 5 | 5 | 5 |
| 3.7 | 0.25 | 5 | 5 | 5 | 5 | 5 | 5 | 5 | 5 |
| | 0.5 | 5 | 5 | 5 | 5 | 5 | 5 | 5 | 5 |
| 3.8 | 0.25 | 5 | 5 | 5 | 5 | 5 | 5 | 5 | 5 |
| | 0.5 | 5 | 5 | 5 | 5 | 5 | 5 | 5 | 5 |
| 3.10 | 0.25 | 5 | 5 | 5 | 5 | 5 | 5 | 5 | 5 |
| | 0.5 | 5 | 5 | 5 | 5 | 5 | 5 | 5 | 5 |
| 3.12 | 0.25 | 5 | 5 | 5 | 5 | 5 | 5 | 5 | 5 |
| | 0.5 | 5 | 5 | 5 | 5 | 5 | 5 | 5 | 5 |
| 3.13 | 0.25 | 5 | 5 | 5 | 5 | 5 | 5 | 5 | 5 |
| | 0.5 | 5 | 5 | 5 | 5 | 5 | 5 | 5 | 5 |
| 3.14 | 0.25 | 5 | 5 | 5 | 5 | 5 | 5 | 5 | 5 |
| | 0.5 | 5 | 5 | 5 | 5 | 5 | 5 | 5 | 5 |
| 3.16 | 0.25 | 5 | 5 | 5 | 5 | 5 | 5 | 5 | 5 |
| | 0.5 | 5 | 5 | 5 | 5 | 5 | 5 | 5 | 5 |
| 3.17 | 0.25 | 5 | 5 | 5 | 5 | 5 | 5 | 5 | 5 |
| | 0.5 | 5 | 5 | 5 | 5 | 5 | 5 | 5 | 5 |
| Control A | 1.0 | 5 | 5 | 5 | 5 | 4 | 5 | 4 | 3 |
| | 0.5 | 4 | 4 | 4 | 3 | 3 | 4 | 3 | 2 |
| | 0.25 | 3 | 3 | 3 | 2 | 2 | 2 | 2 | 1 |
| | 0.125 | 2 | 2 | 1 | 1 | 1 | 1 | 1 | 0 |
| Control B | 1.0 | 4 | 4 | 4 | 4 | 3 | 5 | 2 | 1 |
| | 0.5 | 3 | 3 | 3 | 3 | 2 | 4 | 1 | 0 |
| | 0.25 | 2 | 2 | 2 | 2 | 1 | 2 | 0 | 0 |
| | 0.125 | 1 | 1 | 1 | 1 | 0 | 1 | 0 | 0 |
| Control C | 1.0 | 5 | 4 | 5 | 4 | 4 | 4 | 4 | 3 |
| | 0.5 | 4 | 3 | 4 | 3 | 3 | 3 | 3 | 2 |
| | 0.25 | 3 | 3 | 3 | 2 | 2 | 2 | 2 | 1 |
| | 0.125 | 2 | 2 | 2 | 1 | 1 | 1 | 1 | 0 |
| Control D | 1.0 | 5 | 5 | 5 | 4 | 4 | 5 | 5 | 4 |
| | 0.5 | 4 | 4 | 4 | 3 | 3 | 4 | 4 | 3 |
| | 0.25 | 3 | 3 | 3 | 2 | 2 | 2 | 3 | 2 |

TABLE 7-continued

| Compound No. | Application dosage (Kg/ha) | Annual weed | | | | Perennial weed | | | |
| --- | --- | --- | --- | --- | --- | --- | --- | --- | --- |
| | | barnyardgrass (*Echinochloa crus-galli*) | ducksalad (*Monochoria vaginalis*) | false pimpernel (*Lindernia procumbens*) | toothcup (*Rotala indica*) | bulrush (*Scirpus hotarui*) | arrowhead (*Sagittaria pygmaea*) | perennial flat sedge (*Cyperus serotinus*) | perennial spikerush (*Eleocharis kuroguwai*) |
| | 0.125 | 2 | 2 | 1 | 1 | 1 | 1 | 2 | 1 |
| Control E | 0.5 | 3 | 4 | 4 | 4 | 4 | 4 | 4 | 3 |
| | 0.25 | 3 | 4 | 4 | 4 | 3 | 4 | 3 | 3 |
| Control F | 0.5 | 4 | 4 | 4 | 3 | 3 | 4 | 3 | 2 |
| | 0.25 | 4 | 3 | 3 | 2 | 2 | 2 | 2 | 1 |
| | 0.125 | 3 | 2 | 1 | 1 | 1 | 1 | 1 | 0 |

*Control A:

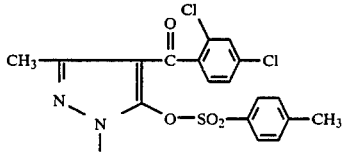

(compound according to U.S. Pat. Nos. 4,063,925 and 4,146,726)

*Control B:

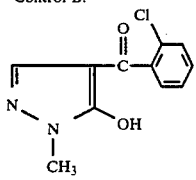

(compound according to U.S. Pat. Nos. 4,063,925 and 4,146,726)

*Control C:

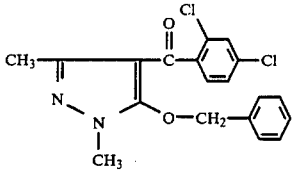

*Control D:

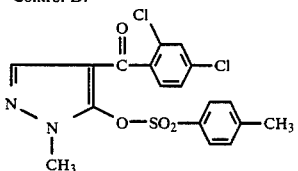

*Control E:

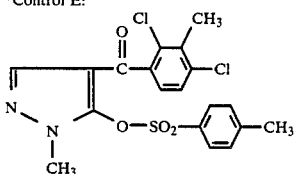

*Control F:

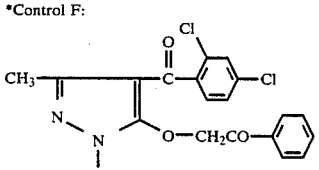

(compound according to U.S. Pat. No. 4,230,481)

As obvious from Table 7, the compounds according to the present invention exhibit powerful herbicidal effects upon the annual weeds as well as the perennial weeds, while the control compounds rapidly decrease their herbicidal effects with the decrease in the application dosage.

Test Example 2: Herbicidal effect test (2) in Submerged conditions

After a certain amount of alluvial soil was placed in a Wagner pot of 1/5,000 are (a), water was added thereto to obtain a submerged state of 2 cm in water depth through well mixing. Then, tubers of perennial flat sedge (*Cyperus serotinus*) and perennial spikerush (*Eleocharis kuroguwai*) which had been picked at previous year from the perrenial weed frequently occuring paddy field were planted in the submerged soil in the Wagner pot, and seeds of bulrush (*Scirpus hotarui*) were scatteredly sowed. Immediately after germination took place, a predetermined amount of diluted solution containing the compound according to the present invention was added dropwise by means of a measuring pipette over the water surface of the soil.

Three weeks later after the application, the weights of the live plants were measured, and the herbicidal rates were calculated in the same manner as in the case of Test Example 1. In such calculation, the whitened portions of the plants were considered to be withered. The results are shown in Table 8.

TABLE 8

| Compound No. | Application dosage (Kg/ha) | bulrush (Scirpus hotarui) | perennial flat sedge (Cyperus serotinus) | perennial spikerush (Eleocharis kuroguwai) |
|---|---|---|---|---|
| 1.1 | 0.5 | 100 | 100 | 100 |
| | 0.25 | 100 | 100 | 100 |
| | 0.125 | 100 | 100 | 100 |
| | 0.0625 | 100 | 100 | 100 |
| 1.2 | 0.5 | 100 | 100 | 100 |
| | 0.25 | 100 | 100 | 100 |
| | 0.125 | 100 | 100 | 100 |
| | 0.0625 | 100 | 100 | 100 |
| 1.3 | 0.5 | 100 | 100 | 100 |
| | 0.25 | 100 | 100 | 100 |
| | 0.125 | 100 | 100 | 100 |
| | 0.0625 | 100 | 100 | 100 |
| 1.4 | 0.5 | 100 | 100 | 100 |
| | 0.25 | 100 | 100 | 100 |
| | 0.125 | 100 | 100 | 100 |
| | 0.0625 | 100 | 100 | 100 |
| 1.5 | 0.5 | 100 | 100 | 100 |
| | 0.25 | 100 | 100 | 100 |
| | 0.125 | 100 | 100 | 100 |
| | 0.0625 | 100 | 100 | 100 |
| 1.6 | 0.5 | 100 | 100 | 100 |
| | 0.25 | 100 | 100 | 100 |
| | 0.125 | 100 | 100 | 100 |
| | 0.0625 | 100 | 100 | 100 |
| 1.7 | 0.5 | 100 | 100 | 100 |
| | 0.25 | 100 | 100 | 100 |
| | 0.125 | 100 | 100 | 100 |
| | 0.0625 | 100 | 100 | 100 |
| 1.8 | 0.5 | 100 | 100 | 100 |
| | 0.25 | 100 | 100 | 100 |
| | 0.125 | 100 | 100 | 100 |
| | 0.0625 | 100 | 100 | 100 |
| 1.9 | 0.5 | 100 | 100 | 100 |
| | 0.25 | 100 | 100 | 100 |
| | 0.125 | 100 | 100 | 100 |
| | 0.0625 | 100 | 100 | 100 |
| 1.10 | 0.5 | 100 | 100 | 100 |
| | 0.25 | 100 | 100 | 100 |
| | 0.125 | 100 | 100 | 100 |
| | 0.0625 | 100 | 100 | 100 |
| 1.11 | 0.5 | 100 | 100 | 100 |
| | 0.25 | 100 | 100 | 100 |
| | 0.125 | 100 | 100 | 100 |
| | 0.0625 | 100 | 100 | 100 |
| 1.12 | 0.5 | 100 | 100 | 100 |
| | 0.25 | 100 | 100 | 100 |
| | 0.125 | 100 | 100 | 100 |
| | 0.0625 | 100 | 100 | 100 |
| 1.13 | 0.5 | 100 | 100 | 100 |
| | 0.25 | 100 | 100 | 100 |
| | 0.125 | 100 | 100 | 100 |
| | 0.0625 | 100 | 100 | 100 |
| 1.14 | 0.5 | 100 | 100 | 100 |
| | 0.25 | 100 | 100 | 100 |
| | 0.125 | 100 | 100 | 100 |
| | 0.0625 | 100 | 100 | 100 |
| 1.15 | 0.5 | 100 | 100 | 100 |
| | 0.25 | 100 | 100 | 100 |
| | 0.125 | 100 | 100 | 100 |
| | 0.0625 | 100 | 100 | 100 |
| 1.16 | 0.5 | 100 | 100 | 100 |
| | 0.25 | 100 | 100 | 100 |
| | 0.125 | 100 | 100 | 100 |
| | 0.0625 | 100 | 100 | 100 |
| 1.18 | 0.5 | 100 | 100 | 100 |
| | 0.25 | 100 | 100 | 100 |
| | 0.125 | 100 | 100 | 100 |
| | 0.0625 | 100 | 100 | 100 |
| 1.19 | 0.5 | 100 | 100 | 100 |
| | 0.25 | 100 | 100 | 100 |
| | 0.125 | 100 | 100 | 100 |
| | 0.0625 | 100 | 100 | 100 |
| 1.20 | 0.5 | 100 | 100 | 100 |
| | 0.25 | 100 | 100 | 100 |
| | 0.125 | 100 | 100 | 100 |
| | 0.0625 | 100 | 100 | 100 |
| 1.21 | 0.5 | 100 | 100 | 100 |
| | 0.25 | 100 | 100 | 100 |
| | 0.125 | 100 | 100 | 100 |
| | 0.0625 | 100 | 100 | 100 |
| 1.27 | 0.5 | 100 | 100 | 100 |
| | 0.25 | 100 | 100 | 100 |
| | 0.125 | 100 | 100 | 100 |
| | 0.0625 | 100 | 100 | 100 |
| 1.50 | 0.5 | 100 | 100 | 100 |
| | 0.25 | 100 | 100 | 100 |
| | 0.125 | 100 | 100 | 100 |
| | 0.0625 | 100 | 100 | 100 |
| 1.51 | 0.5 | 100 | 100 | 100 |
| | 0.25 | 100 | 100 | 100 |
| | 0.125 | 100 | 100 | 100 |
| | 0.0625 | 100 | 100 | 100 |
| 1.54 | 0.5 | 100 | 100 | 100 |
| | 0.25 | 100 | 100 | 100 |
| | 0.125 | 100 | 100 | 100 |
| | 0.0625 | 100 | 100 | 100 |
| 1.55 | 0.5 | 100 | 100 | 100 |
| | 0.25 | 100 | 100 | 100 |
| | 0.125 | 100 | 100 | 100 |
| | 0.0625 | 100 | 100 | 100 |
| 2.1 | 0.5 | 100 | 100 | 100 |
| | 0.25 | 100 | 100 | 100 |
| | 0.125 | 85 | 100 | 100 |
| 2.2 | 0.5 | 100 | 100 | 100 |
| | 0.25 | 100 | 100 | 100 |
| | 0.125 | 100 | 100 | 100 |
| 2.3 | 0.5 | 100 | 100 | 100 |
| | 0.25 | 100 | 100 | 100 |
| | 0.125 | 100 | 100 | 100 |
| 2.4 | 0.5 | 100 | 100 | 100 |
| | 0.25 | 100 | 100 | 100 |
| | 0.125 | 100 | 100 | 100 |
| 2.5 | 0.5 | 100 | 100 | 100 |
| | 0.25 | 100 | 100 | 100 |
| | 0.125 | 100 | 100 | 100 |
| 2.6 | 0.5 | 100 | 100 | 100 |
| | 0.25 | 100 | 100 | 100 |
| | 0.125 | 100 | 100 | 100 |
| 2.7 | 0.5 | 100 | 100 | 100 |
| | 0.25 | 100 | 100 | 100 |
| | 0.125 | 100 | 100 | 100 |
| 2.8 | 0.5 | 100 | 100 | 100 |
| | 0.25 | 100 | 100 | 100 |
| | 0.125 | 100 | 100 | 100 |
| 2.9 | 0.5 | 100 | 100 | 100 |
| | 0.25 | 100 | 100 | 100 |
| | 0.125 | 100 | 100 | 100 |
| 2.10 | 0.5 | 100 | 100 | 100 |
| | 0.25 | 100 | 100 | 100 |
| | 0.125 | 100 | 100 | 100 |
| 2.11 | 0.5 | 100 | 100 | 100 |
| | 0.25 | 100 | 100 | 100 |
| | 0.125 | 100 | 100 | 100 |
| 2.13 | 0.5 | 100 | 100 | 100 |
| | 0.25 | 100 | 100 | 100 |
| | 0.125 | 100 | 100 | 100 |
| 2.14 | 0.5 | 100 | 100 | 100 |
| | 0.25 | 100 | 100 | 100 |
| | 0.125 | 100 | 100 | 100 |
| 2.15 | 0.5 | 100 | 100 | 100 |
| | 0.25 | 100 | 100 | 100 |
| | 0.125 | 100 | 100 | 100 |
| 2.16 | 0.5 | 100 | 100 | 100 |

TABLE 8-continued

| Compound No. | Application dosage (Kg/ha) | bulrush (Scirpus hotarui) | perennial flat sedge (Cyperus serotinus) | perennial spikerush (Eleocharis kuroguwai) |
|---|---|---|---|---|
| | 0.25 | 100 | 100 | 100 |
| | 0.125 | 100 | 100 | 100 |
| 2.17 | 0.5 | 100 | 100 | 100 |
| | 0.25 | 100 | 100 | 100 |
| | 0.125 | 100 | 100 | 100 |
| 2.18 | 0.5 | 100 | 100 | 100 |
| | 0.25 | 100 | 100 | 100 |
| | 0.125 | 100 | 100 | 100 |
| 2.19 | 0.5 | 100 | 100 | 100 |
| | 0.25 | 100 | 100 | 100 |
| | 0.125 | 100 | 100 | 100 |
| 2.20 | 0.5 | 100 | 100 | 100 |
| | 0.25 | 100 | 100 | 100 |
| | 0.125 | 100 | 100 | 100 |
| 3.1 | 0.5 | 100 | 100 | 100 |
| | 0.25 | 100 | 100 | 100 |
| 3.2 | 0.5 | 100 | 100 | 100 |
| | 0.25 | 100 | 100 | 100 |
| 3.3 | 0.5 | 100 | 100 | 100 |
| | 0.25 | 100 | 100 | 100 |
| 3.4 | 0.5 | 100 | 100 | 100 |
| | 0.25 | 100 | 100 | 100 |
| 3.5 | 0.5 | 100 | 100 | 100 |
| | 0.25 | 100 | 100 | 100 |
| 3.7 | 0.5 | 100 | 100 | 100 |
| | 0.25 | 100 | 100 | 100 |
| 3.8 | 0.5 | 100 | 100 | 100 |
| | 0.25 | 100 | 100 | 100 |
| 3.10 | 0.5 | 100 | 100 | 100 |
| | 0.25 | 100 | 100 | 100 |
| 3.12 | 0.5 | 100 | 100 | 100 |
| | 0.25 | 100 | 100 | 100 |
| 3.13 | 0.5 | 100 | 100 | 100 |
| | 0.25 | 100 | 100 | 100 |
| 3.14 | 0.5 | 100 | 100 | 100 |
| | 0.25 | 100 | 100 | 100 |
| 3.16 | 0.5 | 100 | 100 | 100 |
| | 0.25 | 100 | 100 | 100 |
| 3.17 | 0.5 | 100 | 100 | 100 |
| | 0.25 | 100 | 100 | 100 |
| Control A | 0.5 | 60 | 55 | 25 |
| | 0.25 | 28 | 20 | 10 |
| | 0.125 | 12 | 5 | 0 |
| | 0.0625 | 0 | 0 | — |
| Control B | 0.5 | 45 | 35 | 5 |
| | 0.25 | 20 | 10 | 0 |
| | 0.125 | 5 | 0 | 0 |
| | 0.0625 | 0 | 0 | 0 |
| Control C | 0.4 | 55 | 50 | 18 |
| | 0.25 | 25 | 22 | 0 |
| | 0.125 | 5 | 8 | 0 |
| | 0.0625 | 0 | 0 | 0 |
| Control D | 0.5 | 65 | 80 | 65 |
| | 0.25 | 30 | 55 | 35 |
| | 0.125 | 10 | 25 | 15 |
| | 0.0625 | 0 | 10 | 0 |

Controls A, B, C and D appearing in Table 8 are the same as in Test Example 1. As obvious from Table 8, the compounds according to the present invention exhibit powerful herbicidal effects even in a lower application dosages upon bulrush (*Scirpus hotarui*), perennial flat sedge (*Cyperus serotinus*), perennial spikerush (*Eleocharis kuroguwai*) in the paddy field which show stout resistance against the conventional herbicides, while the control compounds decrease their herbicidal effects with the decrease in the application dosages.

Test Example 3: Phytotoxity in rice plant in submerged conditions

After a certain amount of alluviate soil was placed in a Neubauer pot of 1/10,000 are (a), water was added thereto to obtain a submerged state of 2 cm in water depth through kneading.

After a predetermined amount of a diluted solution containing each compound according to the present invention was added dropwise over the water surface of the soil, the soil within 2 cm in depth from the surface of the soil was stirred. Two days after the stirring, 2.5 leaf stage of rice plants (variety: Nihon Bare) which had grown preliminarily in a rice plant cultivator were transplanted at three locations in the Neubauer pot in which two pieces of the rice plants were planted. One month after the transplantation, the growing states of the rice plants were observed. The tests were conducted with respect to the areas where 5 kg/ha, and 2.5 kg/ha of each compounds according to the present invention were applied.

The growing states as to the height and number of the rice plants were substantially the same as in all the non-treated areas. Further, no chlorosis (whitening) was observed in the rice plants, and no phytotoxity was confirmed.

The results are shown in Table 9.

TABLE 9

| Compound No. | Application dosage (kg/ha) | Phytotoxity | Compound No. | Application dosage (kg/ha) | Phytotoxity |
|---|---|---|---|---|---|
| 1.1 | 5.0 | 0 | 1.6 | 5.0 | 0 |
| | 2.5 | 0 | | 2.5 | 0 |
| 1.2 | 5.0 | 0 | 1.7 | 5.0 | 0 |
| | 2.5 | 0 | | 2.5 | 0 |
| 1.3 | 5.0 | 0 | 1.9 | 5.0 | 0 |
| | 2.5 | 0 | | 2.5 | 0 |
| 1.10 | 5.0 | 0 | 2.1 | 5.0 | 0 |
| | 2.5 | 0 | | 2.5 | 0 |
| 1.11 | 5.0 | 0 | 2.2 | 5.0 | 0 |
| | 2.5 | 0 | | 2.5 | 0 |
| 1.12 | 5.0 | 0 | 2.3 | 5.0 | 0 |
| | 2.5 | 0 | | 2.5 | 0 |
| 1.16 | 5.0 | 0 | 2.4 | 5.0 | 0 |
| | 2.5 | 0 | | 2.5 | 0 |
| 1.18 | 5.0 | 0 | 2.5 | 5.0 | 0 |
| | 2.5 | 0 | | 2.5 | 0 |
| 1.19 | 5.0 | 0 | 2.6 | 5.0 | 0 |
| | 2.5 | 0 | | 2.5 | 0 |
| 1.20 | 5.0 | 0 | 2.7 | 5.0 | 0 |
| | 2.5 | 0 | | 2.5 | 0 |
| 1.21 | 5.0 | 0 | 2.8 | 5.0 | 0 |
| | 2.5 | 0 | | 2.5 | 0 |
| 1.27 | 5.0 | 0 | 2.9 | 5.0 | 0 |
| | 2.5 | 0 | | 2.5 | 0 |
| 1.50 | 5.0 | 0 | 2.10 | 5.0 | 0 |
| | 2.5 | 0 | | 2.5 | 0 |
| 1.51 | 5.0 | 0 | 2.11 | 5.0 | 0 |
| | 2.5 | 0 | | 2.5 | 0 |
| 1.54 | 5.0 | 0 | 2.13 | 5.0 | 0 |
| | 2.5 | 0 | | 2.5 | 0 |
| 1.55 | 5.0 | 0 | 2.14 | 5.0 | 0 |
| | 2.5 | 0 | | 2.5 | 0 |
| 2.15 | 5.0 | 0 | 3.7 | 2.5 | 0 |
| | 2.5 | 0 | | 1.25 | 0 |
| 2.16 | 5.0 | 0 | 3.8 | 2.5 | 0 |
| | 2.5 | 0 | | 1.25 | 0 |
| 2.17 | 5.0 | 0 | 3.10 | 2.5 | 0 |
| | 2.5 | 0 | | 1.25 | 0 |
| 2.18 | 5.0 | 0 | 3.12 | 2.5 | 0 |
| | 2.5 | 0 | | 1.25 | 0 |
| 2.19 | 5.0 | 0 | 3.13 | 2.5 | 0 |
| | 2.5 | 0 | | 1.25 | 0 |
| 2.20 | 5.0 | 0 | 3.14 | 2.5 | 0 |
| | 2.5 | 0 | | 1.25 | 0 |
| 3.1 | 2.5 | 0 | 3.16 | 2.5 | 0 |
| | 1.25 | 0 | | 1.25 | 0 |
| 3.2 | 2.5 | 0 | 3.17 | 2.5 | 0 |
| | 1.25 | 0 | | 1.25 | 0 |
| 3.3 | 2.5 | 0 | *Control D | 5.0 | 4 |
| | 1.25 | 0 | | 2.5 | 3 |
| | | | | 1.25 | 3 |
| 3.4 | 2.5 | 0 | *Control E | 2.5 | 4 |
| | 1.25 | 0 | | 1.25 | 3 |
| 3.5 | 2.5 | 0 | | | |

TABLE 9-continued

| Compound No. | Application dosage (kg/ha) | Phytotoxicity | Compound No. | Application dosage (kg/ha) | Phytotoxicity |
|---|---|---|---|---|---|
| | 1.25 | 0 | | | |

Evaluation Standard:
5 . . . almost completely withered
4 . . . remarkable phytotoxity against crops
3 . . . recognizable phytotoxity against crops
2 . . . slightly recognizable phytotoxity against crops
1 . . . almost no phytotoxity against crops
0 . . . no phytotoxity against crops Compounds D and E as controls are the same as employed in Test Example 1.

As seen from Table 9, the compounds according to the present invention exhibited no phytotoxity against paddy-rice plants even at high application dosage, while Control Compounds D and E exhibited conspicurous phytotoxity against the crops.

What is claimed is:

1. A pyrazole derivative of the formula I:

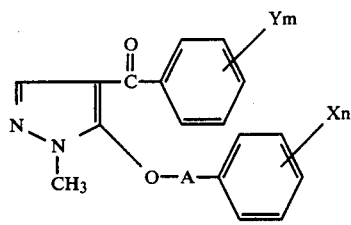

wherein, A denotes a straight or branched lower alkylene or lower alkylidene group; X denotes a halogen atom, nitro group, a lower alkyl group, a lower haloalkyl group, a lower alkoxy group, a lower haloalkoxy group, a lower alkenyl group, phenyl group, cyano group, phenoxy group, a lower alkoxycarbonyl group, a straight or branched alkanoyl group having 2 to 5 carbon atoms, a benzoyl group, methanesulfonyloxy group or group

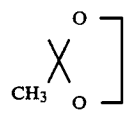

and n is 0 or an integer of 1 to 5; said Xs being the same or different when n is an integer of 2 to 5; and Y denotes a halogen atom, a lower alkyl group, nitro group, phenyl group, a lower alkoxy group or trifluoromethyl group and m is an integer of 1 to 3, said Ys being the same or different when m is 2 or 3.

2. A compound according to claim 1, wherein the compound is represented by the formula IA:

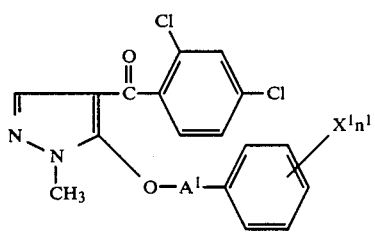

wherein, $A^1$ denotes a straight or branched lower alkylene or lower alkylidene group, $X^1$ denotes a halogen atom, nitro group or a lower alkyl group and $n^1$ is 0 or an integer of 1 to 5, said $X^1$s being the same or different when $n^1$ is an integer of 2 to 5.

3. A compound according to claim 1, wherein the compound is represented by the formula IB:

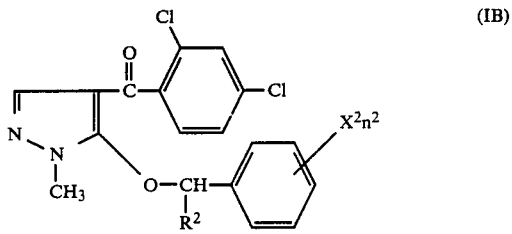

wherein, $R^2$ denotes hydrogen atom or a lower alkyl group; and $X^2$ denotes a lower haloalkyl group, a lower alkoxy group, a lower haloalkoxy group, a lower alkenyl group, phenyl group, cyano group, phenoxy group, a lower alkoxycarbonyl group, a straight or branched alkanoyl group having 2 to 5 carbon atoms, a benzoyl group, methanesulfonyloxy group or a group

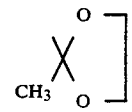

and $n^2$ is an integer of 1 to 3, $X^2$s being the same or different when $n^2$ is 2 or 3.

4. A compound according to claim 1, wherein the compound is represented by the formula IC:

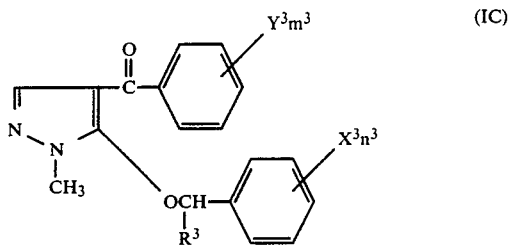

wherein, $R^3$ denotes hydrogen atom or a lower alkyl group; $X^3$ denotes a halogen atom, a lower alkyl group, a lower haloalkyl group, a lower alkoxy group, a lower haloalkoxy group, a lower alkenyl group, or nitro group and $n^3$ is 0 or an integer of 1 to 3, said $X^3$s being the same or different when $n^3$ is 2 or 3; and $Y^3$ is a halogen atom, a lower alkyl group, nitro group, phenyl group, a lower alkoxy group, or trifluoromethyl group and $m^3$ is an integer of 1 to 3, said $Y^3$s being the same or different when $m^3$ is 2 or 3.

5. A pyrazole derivative of the formula:

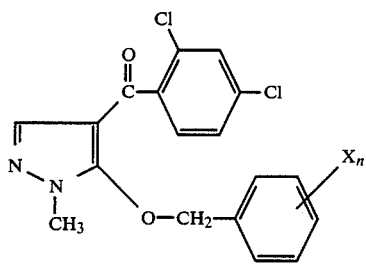

wherein X is a member selected from the group consisting of CH₃, C₂H₅, P, Cl, Br and NO₂ and n is 0, 1 or 2, said Xs being the same or different when n is 2.

6. A pyrazole derivative of claim 1 having the formula:

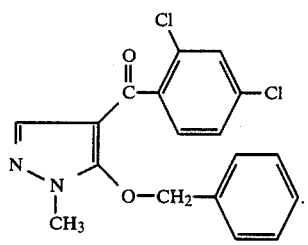

7. A pyrazole derivative of claim 1 having the formula:

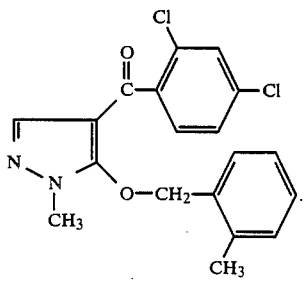

8. A pyrazole derivative of claim 1 having the formula:

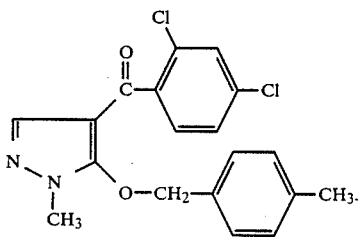

9. A pyrazole derivative of claim 1 having the formula:

10. A pyrazole derivative of claim 1 having the formula:

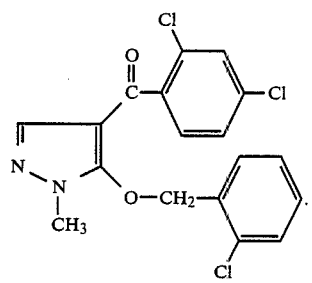

11. A pyrazole derivative of claim 1 having the formula:

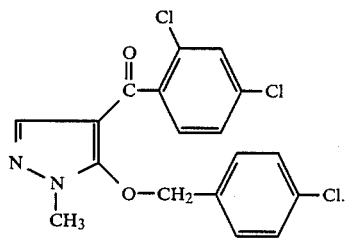

12. A pyrazole derivative of claim 1 having the formula:

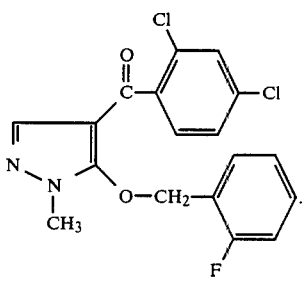

13. A pyrazole derivative of claim 1 having the formula:

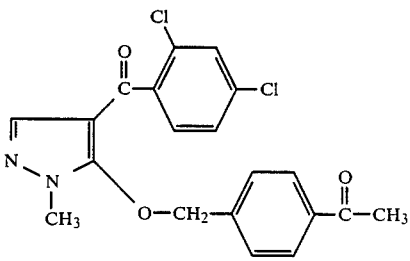

14. A pyrazole derivative of claim 1 having the formula:

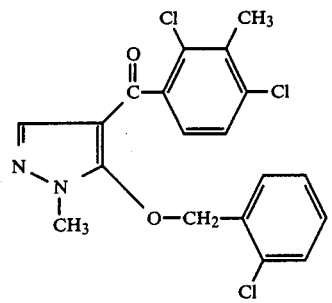

15. A pyrazole derivative of claim 1 having the formula:

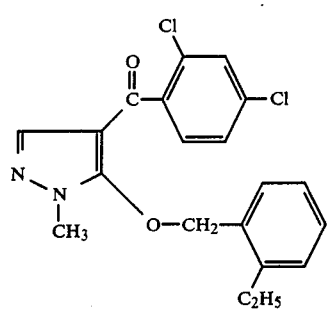

16. A pyrazole derivative of claim 1 having the formula:

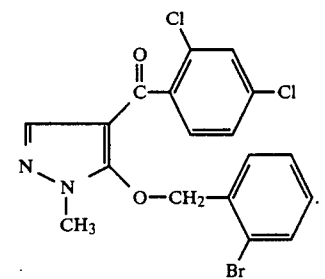

17. A pyrazole derivative of claim 1 having the formula:

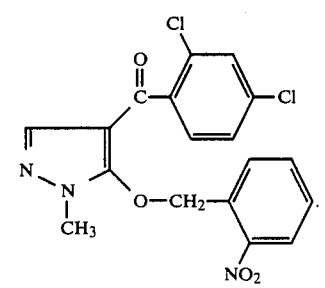

18. A pyrazole derivative of claim 1 having the formula:

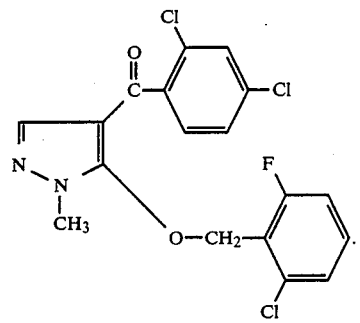

19. A selective herbicidal composition containing as active ingredient a herbicidally effective amount of one or more of the compounds of the formula I:

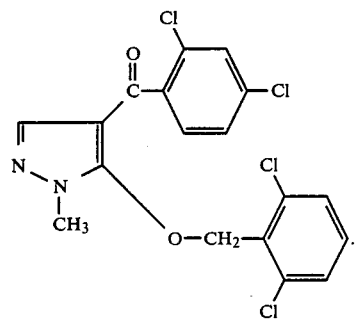

wherein, A denotes a straight or branched lower alkylene or lower alkylidene group; X denotes a halogen atom, nitro group, a lower alkyl group, a lower haloalkyl group, a lower alkoxy group, a lower haloalkoxy group, a lower alkenyl, phenyl group, cyano group, phenoxy group, a lower alkoxycarbonyl group, a straight or branched alkanoyl group having 2 to 5 carbon atoms, a benzoyl group, methanesulfonyloxy group or group

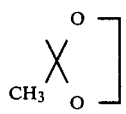

and n is 0 or an integer of 1 to 5, said Xs being the same or different when n is an integer of 2 to 5; and Y denotes a halogen atom, a lower alkyl group, nitro group, phenyl group, a lower alkoxy group or trifluoromethyl group and m is an integer of 1 to 3, said Ys being the same or different when m is 2 or 3, together with a carrier therefor.

20. A herbicidal composition according to claim 19, wherein the active compound is represented by the formula IA:

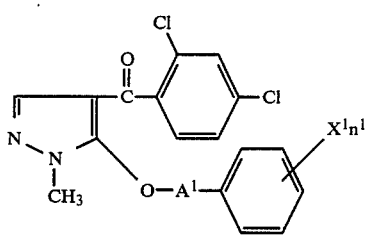

wherein, $A^1$ denotes a straight or branched lower alkylene or lower alkylidene group, $X^1$ denotes a halogen atom, nitro group or a lower alkyl group and $n^1$ is 0 or an integer of 1 to 5, said $X^1$s being the same or different when $n^1$ is an integer of 2 to 5.

21. A herbicidal composition according to claim 19, wherein the active compound is represented by the formula IB:

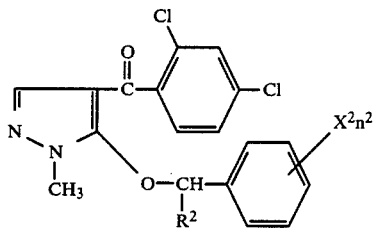

wherein, $R^2$ denotes hydrogen atom or a lower alkyl group; and $X^2$ denotes a lower haloalkyl group, a lower alkoxy group, a lower haloalkoxy group, a lower alkenyl group, phenyl group, cyano group, phenoxy group, a lower alkoxycarbonyl group a straight or branched alkanoyl group having 2 to 5 carbon atoms, a benzoyl group, methanesulfonyloxy group or a group

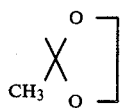

and $n^2$ is an integer of 1 to 3, $X^2$s being the same or different when $n^2$ is 2 or 3.

22. A herbicidal composition according to claim 19, wherein the active compound is represented by the formula 10:

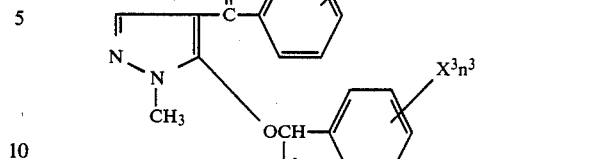

wherein $R^3$ denotes hydrogen atom or a lower alkyl group; $X^3$ denotes a halogen atom, a lower alkyl group, a lower haloalkyl group, a lower alkoxy group, a lower haloalkoxy group, a lower alkenyl group, or nitro group and $n^3$ is 0 or an integer of 1 to 3, said $X^3$s being the same or different when $n^3$ is 2 or 3, and $Y^3$ is a halogen atom, a lower alkyl group, nitro group, phenyl group, a lower alkoxy group, or trifluoromethyl group and $m^3$ is an integer of 1 to 3, said $Y^3$s being the same or different when $m^3$ is 2 or 3.

23. A method of damaging and controlling weeds which comprises applying to the weeds or to the locus thereof a herbicidally effective amount of a compound of the formula I:

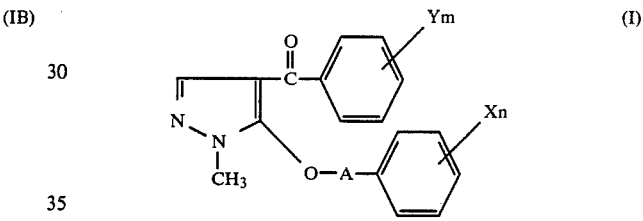

wherein, A denotes a straight or branched lower alkylene or lower alkylidene group, X denotes a halogen atom, nitro group, a lower alkyl group, a lower haloalkyl group, a lower alkoxy group, a lower haloalkoxy group, a lower alkenyl group, phenyl group, cyano group, phenoxy group, a lower alkoxycarbonyl group, a straight or branched alkanoyl group having 2 to 5 carbon atoms, a benzoyl group, methanesulfonyloxy group or group

and n is 0 or an integer of 1 to 5, said Xs being the same or different when n is an integer of 2 to 5; and Y denotes a halogen atom, a lower alkyl group, nitro group, phenyl group, a lower alkoxy group or trifluoromethyl group and m is an integer of 1 to 3, said Ys being the same or different when m is 2 or 3.

* * * * *

UNITED STATES PATENT OFFICE
CERTIFICATE OF CORRECTION

Patent No. 4,557,753      Dated December 10, 1985

Inventor(s) TANAKA ET AL

It is certified that error appears in the above-identified patent and that said Letters Patent are hereby corrected as shown below:

Claim 5, Column 69, Line 16, for "P" read --F--.

Claim 22, Column 73, Line 58, for the numeral "10" read --IC--.

Signed and Sealed this

First Day of April 1986

[SEAL]

Attest:

Attesting Officer

DONALD J. QUIGG

Commissioner of Patents and Trademarks